US008965498B2

(12) United States Patent  (10) Patent No.: US 8,965,498 B2
Katra et al.  (45) Date of Patent: Feb. 24, 2015

(54) METHOD AND APPARATUS FOR PERSONALIZED PHYSIOLOGIC PARAMETERS

(75) Inventors: Rodolphe Katra, Blaine, MN (US); Niranjan Chakravarthy, Minneapolis, MN (US); Imad Libbus, St. Paul, MN (US)

(73) Assignee: Corventis, Inc., St. Paul, MN (US)

( * ) Notice: Subject to any disclaimer, the term of this patent is extended or adjusted under 35 U.S.C. 154(b) by 524 days.

(21) Appl. No.: 13/073,745

(22) Filed: Mar. 28, 2011

(65) Prior Publication Data

US 2011/0245711 A1  Oct. 6, 2011

Related U.S. Application Data

(60) Provisional application No. 61/321,040, filed on Apr. 5, 2010.

(51) Int. Cl.
*A61B 5/05* (2006.01)
*A61B 5/0205* (2006.01)
(Continued)

(52) U.S. Cl.
CPC ............. *A61B 5/0205* (2013.01); *A61B 5/1079* (2013.01); *A61B 5/6833* (2013.01); *A61B 5/1072* (2013.01); *A61B 5/4872* (2013.01);
(Continued)

(58) Field of Classification Search
USPC ........................... 600/382, 481, 506, 529, 547
See application file for complete search history.

(56) References Cited

U.S. PATENT DOCUMENTS 834,261 A  10/1906  Chambers
2,087,124 A  7/1937  Smith et al.
(Continued)

FOREIGN PATENT DOCUMENTS

WO      98/51211 A1    11/1998
WO   WO 00/79255 A1   12/2000
(Continued)

OTHER PUBLICATIONS

"Acute Decompensated Heart Failure"—Wikipedia Entry, downloaded from: <http://en.wikipedia.org/wiki/Acute_decompensated_heart_failure>, entry page created in 2008, 6 pages total.

(Continued)

*Primary Examiner* — Rene Towa
(74) *Attorney, Agent, or Firm* — Billion & Armitage

(57) ABSTRACT

Methods and apparatus combine patient measurement data with demographic or physiological data of the patient to determine an output that can be used to diagnose and treat the patient. A customized output can be determined based the demographics of the patient, physiological data of the patient, and data of a population of patients. In another aspect, patient measurement data is used to predict an impending cardiac event, such as acute decompensated heart failure. At least one personalized value is determined for the patient, and a patient event prediction output is generated based at least in part on the personalized value and the measurement data. For example, bioimpedance data may be used to establish a baseline impedance specific to the patient, and the patient event prediction output generated based in part on the relationship of ongoing impedance measurements to the baseline impedance. Multivariate prediction models may enhance prediction accuracy.

19 Claims, 18 Drawing Sheets

(51) Int. Cl.
*A61B 5/107* (2006.01)
*A61B 5/00* (2006.01)
*A61B 6/00* (2006.01)
*A61B 5/053* (2006.01)
*A61N 1/00* (2006.01)

(52) U.S. Cl.
CPC ............ *A61B 5/0075* (2013.01); *A61B 5/1073* (2013.01); *A61B 6/482* (2013.01); *A61B 5/0004* (2013.01); *A61B 5/0537* (2013.01); *A61B 5/4878* (2013.01); *A61B 5/4875* (2013.01); *A61B 5/7225* (2013.01); *A61B 5/1075* (2013.01); *A61B 5/7282* (2013.01); *A61N 1/00* (2013.01)
USPC ............ 600/547; 600/382; 600/481; 600/529

(56) References Cited

U.S. PATENT DOCUMENTS

| | | |
|---|---|---|
| 2,184,511 A | 12/1939 | Bagno et al. |
| 3,170,459 A | 2/1965 | Phipps et al. |
| 3,232,291 A | 2/1966 | Parker |
| 3,370,459 A | 2/1968 | Cescati |
| 3,517,999 A | 6/1970 | Weaver |
| 3,620,216 A | 11/1971 | Szymanski |
| 3,677,260 A | 7/1972 | Funfstuck et al. |
| 3,805,769 A | 4/1974 | Sessions |
| 3,845,757 A | 11/1974 | Weyer |
| 3,874,368 A | 4/1975 | Asrican |
| 3,882,853 A | 5/1975 | Gofman et al. |
| 3,942,517 A | 3/1976 | Bowles et al. |
| 3,972,329 A | 8/1976 | Kaufman |
| 4,008,712 A | 2/1977 | Nyboer |
| 4,024,312 A | 5/1977 | Korpman |
| 4,077,406 A | 3/1978 | Sandhage et al. |
| 4,121,573 A | 10/1978 | Crovella et al. |
| 4,141,366 A | 2/1979 | Cross, Jr. et al. |
| RE30,101 E | 9/1979 | Kubicek et al. |
| 4,185,621 A | 1/1980 | Morrow |
| 4,216,462 A | 8/1980 | McGrath et al. |
| 4,300,575 A | 11/1981 | Wilson |
| 4,308,872 A | 1/1982 | Watson et al. |
| 4,358,678 A | 11/1982 | Lawrence |
| 4,409,983 A | 10/1983 | Albert |
| 4,450,527 A | 5/1984 | Sramek |
| 4,451,254 A | 5/1984 | Dinius et al. |
| 4,478,223 A | 10/1984 | Allor |
| 4,498,479 A | 2/1985 | Martio et al. |
| 4,522,211 A | 6/1985 | Bare et al. |
| 4,661,103 A | 4/1987 | Harman |
| 4,664,129 A | 5/1987 | Helzel et al. |
| 4,669,480 A | 6/1987 | Hoffman |
| 4,673,387 A | 6/1987 | Phillips et al. |
| 4,681,118 A | 7/1987 | Asai et al. |
| 4,692,685 A | 9/1987 | Blaze |
| 4,699,146 A | 10/1987 | Sieverding |
| 4,721,110 A | 1/1988 | Lampadius |
| 4,730,611 A | 3/1988 | Lamb |
| 4,781,200 A | 11/1988 | Baker |
| 4,793,362 A | 12/1988 | Tedner |
| 4,838,273 A | 6/1989 | Cartmell |
| 4,838,279 A | 6/1989 | Fore |
| 4,850,370 A | 7/1989 | Dower |
| 4,880,004 A | 11/1989 | Baker, Jr. et al. |
| 4,895,163 A | 1/1990 | Libke et al. |
| 4,911,175 A | 3/1990 | Shizgal |
| 4,945,916 A | 8/1990 | Kretschmer et al. |
| 4,955,381 A | 9/1990 | Way et al. |
| 4,966,158 A | 10/1990 | Honma et al. |
| 4,981,139 A | 1/1991 | Pfohl |
| 4,988,335 A | 1/1991 | Prindle et al. |
| 4,989,612 A | 2/1991 | Fore |
| 5,001,632 A | 3/1991 | Hall-Tipping |
| 5,012,810 A | 5/1991 | Strand et al. |
| 5,025,791 A | 6/1991 | Niwa |
| 5,027,824 A | 7/1991 | Dougherty et al. |
| 5,050,612 A | 9/1991 | Matsumura |
| 5,063,937 A | 11/1991 | Ezenwa et al. |
| 5,080,099 A | 1/1992 | Way et al. |
| 5,083,563 A | 1/1992 | Collins |
| 5,086,781 A | 2/1992 | Bookspan |
| 5,113,869 A | 5/1992 | Nappholz et al. |
| 5,125,412 A | 6/1992 | Thornton |
| 5,133,355 A | 7/1992 | Strand et al. |
| 5,140,985 A | 8/1992 | Schroeder et al. |
| 5,150,708 A | 9/1992 | Brooks |
| 5,168,874 A | 12/1992 | Segalowitz |
| 5,226,417 A | 7/1993 | Swedlow et al. |
| 5,241,300 A | 8/1993 | Buschmann |
| 5,257,627 A | 11/1993 | Rapoport |
| 5,271,411 A | 12/1993 | Ripley et al. |
| 5,273,532 A | 12/1993 | Niezink et al. |
| 5,282,840 A | 2/1994 | Hudrlik |
| 5,291,013 A | 3/1994 | Nafarrate et al. |
| 5,297,556 A | 3/1994 | Shankar |
| 5,301,677 A | 4/1994 | Hsung |
| 5,319,363 A | 6/1994 | Welch et al. |
| 5,331,966 A | 7/1994 | Bennett et al. |
| 5,335,664 A | 8/1994 | Nagashima |
| 5,343,869 A | 9/1994 | Pross et al. |
| 5,353,793 A | 10/1994 | Bornn |
| 5,362,069 A | 11/1994 | Hall-Tipping |
| 5,372,141 A | 12/1994 | Gallup et al. |
| 5,375,604 A | 12/1994 | Kelly et al. |
| 5,411,530 A | 5/1995 | Akhtar |
| 5,437,285 A | 8/1995 | Verrier et al. |
| 5,443,073 A | 8/1995 | Wang et al. |
| 5,449,000 A | 9/1995 | Libke et al. |
| 5,450,845 A | 9/1995 | Axelgaard |
| 5,454,377 A | 10/1995 | Dzwonczyk et al. |
| 5,464,012 A | 11/1995 | Falcone |
| 5,469,859 A | 11/1995 | Tsoglin et al. |
| 5,482,036 A | 1/1996 | Diab et al. |
| 5,503,157 A | 4/1996 | Sramek |
| 5,511,548 A | 4/1996 | Raizzi et al. |
| 5,511,553 A | 4/1996 | Segalowitz |
| 5,518,001 A | 5/1996 | Snell |
| 5,523,742 A | 6/1996 | Simkins et al. |
| 5,529,072 A | 6/1996 | Sramek |
| 5,544,661 A | 8/1996 | Davis et al. |
| 5,558,638 A | 9/1996 | Evers et al. |
| 5,560,368 A | 10/1996 | Berger |
| 5,564,429 A | 10/1996 | Bornn et al. |
| 5,564,434 A | 10/1996 | Halperin et al. |
| 5,566,671 A | 10/1996 | Lyons |
| 5,575,284 A | 11/1996 | Athan et al. |
| 5,607,454 A | 3/1997 | Cameron et al. |
| 5,632,272 A | 5/1997 | Diab et al. |
| 5,634,468 A | 6/1997 | Platt et al. |
| 5,642,734 A | 7/1997 | Ruben et al. |
| 5,673,704 A | 10/1997 | Marchlinski et al. |
| 5,678,562 A | 10/1997 | Sellers |
| 5,687,717 A | 11/1997 | Halpern et al. |
| 5,718,234 A | 2/1998 | Warden et al. |
| 5,724,025 A | 3/1998 | Tavori |
| 5,738,107 A | 4/1998 | Martinsen et al. |
| 5,748,103 A | 5/1998 | Flach et al. |
| 5,767,791 A | 6/1998 | Stoop et al. |
| 5,769,793 A | 6/1998 | Pincus et al. |
| 5,772,508 A | 6/1998 | Sugita et al. |
| 5,772,586 A | 6/1998 | Heinonen et al. |
| 5,778,882 A | 7/1998 | Raymond et al. |
| 5,788,643 A | 8/1998 | Feldman |
| 5,803,915 A | 9/1998 | Kremenchugsky et al. |
| 5,807,272 A | 9/1998 | Kun |
| 5,814,079 A | 9/1998 | Kieval et al. |
| 5,817,035 A | 10/1998 | Sullivan |
| 5,833,603 A | 11/1998 | Kovacs et al. |
| 5,836,990 A | 11/1998 | Li |
| 5,855,614 A | 1/1999 | Stevens et al. |
| 5,860,860 A | 1/1999 | Clayman |
| 5,862,802 A | 1/1999 | Bird |
| 5,862,803 A | 1/1999 | Besson et al. |

(56) References Cited

U.S. PATENT DOCUMENTS

| | | |
|---|---|---|
| 5,865,733 A | 2/1999 | Malinouskas et al. |
| 5,876,353 A | 3/1999 | Riff |
| 5,904,708 A | 5/1999 | Goedeke |
| 5,935,079 A | 8/1999 | Swanson et al. |
| 5,941,831 A | 8/1999 | Turcott |
| 5,944,659 A | 8/1999 | Flach et al. |
| 5,949,636 A | 9/1999 | Johnson et al. |
| 5,957,854 A | 9/1999 | Besson et al. |
| 5,957,861 A | 9/1999 | Combs et al. |
| 5,964,703 A | 10/1999 | Goodman et al. |
| 5,970,986 A | 10/1999 | Bolz et al. |
| 5,984,102 A | 11/1999 | Tay |
| 5,987,352 A | 11/1999 | Klein et al. |
| 6,007,532 A | 12/1999 | Netherly |
| 6,027,523 A | 2/2000 | Schmieding |
| 6,045,513 A | 4/2000 | Stone et al. |
| 6,047,203 A | 4/2000 | Sackner et al. |
| 6,047,259 A | 4/2000 | Campbell et al. |
| 6,049,730 A | 4/2000 | Kristbjarnarson |
| 6,050,267 A | 4/2000 | Nardella et al. |
| 6,050,951 A | 4/2000 | Friedman et al. |
| 6,052,615 A | 4/2000 | Feild et al. |
| 6,080,106 A | 6/2000 | Lloyd et al. |
| 6,081,735 A | 6/2000 | Diab et al. |
| 6,095,991 A | 8/2000 | Krausman et al. |
| 6,102,856 A | 8/2000 | Groff et al. |
| 6,104,949 A | 8/2000 | Pitts Crick et al. |
| 6,112,224 A | 8/2000 | Peifer et al. |
| 6,117,077 A | 9/2000 | Del Mar et al. |
| 6,125,297 A | 9/2000 | Siconolfi |
| 6,129,744 A | 10/2000 | Boute |
| 6,141,575 A | 10/2000 | Price |
| 6,144,878 A | 11/2000 | Schroeppel et al. |
| 6,164,284 A | 12/2000 | Schulman et al. |
| 6,181,963 B1 | 1/2001 | Chin et al. |
| 6,185,452 B1 | 2/2001 | Schulman et al. |
| 6,190,313 B1 | 2/2001 | Hinkle |
| 6,190,324 B1 | 2/2001 | Kieval et al. |
| 6,198,394 B1 | 3/2001 | Jacobsen et al. |
| 6,198,955 B1 | 3/2001 | Axelgaard et al. |
| 6,208,894 B1 | 3/2001 | Schulman et al. |
| 6,212,427 B1 | 4/2001 | Hoover |
| 6,213,942 B1 | 4/2001 | Flach et al. |
| 6,225,901 B1 | 5/2001 | Kail, IV |
| 6,245,021 B1 | 6/2001 | Stampfer |
| 6,259,939 B1 | 7/2001 | Rogel |
| 6,272,377 B1 | 8/2001 | Sweeney et al. |
| 6,277,078 B1 | 8/2001 | Porat et al. |
| 6,287,252 B1 | 9/2001 | Lugo |
| 6,289,238 B1 | 9/2001 | Besson et al. |
| 6,290,646 B1 | 9/2001 | Cosentino et al. |
| 6,295,466 B1 | 9/2001 | Ishikawa et al. |
| 6,305,943 B1 | 10/2001 | Pougatchev et al. |
| 6,306,088 B1 | 10/2001 | Krausman et al. |
| 6,308,094 B1 | 10/2001 | Shusterman et al. |
| 6,312,378 B1 | 11/2001 | Bardy |
| 6,315,721 B2 | 11/2001 | Schulman et al. |
| 6,327,487 B1 | 12/2001 | Stratbucker |
| 6,336,903 B1 | 1/2002 | Bardy |
| 6,339,722 B1 | 1/2002 | Heethaar et al. |
| 6,343,140 B1 | 1/2002 | Brooks |
| 6,347,245 B1 | 2/2002 | Lee et al. |
| 6,358,208 B1 | 3/2002 | Lang et al. |
| 6,385,473 B1 | 5/2002 | Haines et al. |
| 6,398,727 B1 | 6/2002 | Bui et al. |
| 6,400,982 B2 | 6/2002 | Sweeney et al. |
| 6,411,853 B1 | 6/2002 | Millot et al. |
| 6,416,471 B1 | 7/2002 | Kumar et al. |
| 6,442,422 B1 | 8/2002 | Duckert |
| 6,450,820 B1 | 9/2002 | Palsson et al. |
| 6,450,953 B1 | 9/2002 | Place et al. |
| 6,454,707 B1 | 9/2002 | Casscells, III et al. |
| 6,454,708 B1 | 9/2002 | Ferguson et al. |
| 6,459,930 B1 | 10/2002 | Takehara et al. |
| 6,463,328 B1 | 10/2002 | John |
| 6,473,640 B1 | 10/2002 | Erlebacher |
| 6,480,733 B1 | 11/2002 | Turcott |
| 6,480,734 B1 | 11/2002 | Zhang et al. |
| 6,490,478 B1 | 12/2002 | Zhang et al. |
| 6,491,647 B1 | 12/2002 | Bridger et al. |
| 6,494,829 B1 | 12/2002 | New, Jr. et al. |
| 6,512,949 B1 | 1/2003 | Combs et al. |
| 6,520,967 B1 | 2/2003 | Cauthen |
| 6,527,711 B1 | 3/2003 | Stivoric et al. |
| 6,527,729 B1 | 3/2003 | Turcott |
| 6,544,173 B2 | 4/2003 | West et al. |
| 6,544,174 B2 | 4/2003 | West et al. |
| 6,551,251 B2 | 4/2003 | Zuckerwar et al. |
| 6,551,252 B2 | 4/2003 | Sackner et al. |
| 6,569,160 B1 | 5/2003 | Goldin et al. |
| 6,572,557 B2 | 6/2003 | Tchou et al. |
| 6,572,636 B1 | 6/2003 | Hagen et al. |
| 6,577,139 B2 | 6/2003 | Cooper |
| 6,577,893 B1 | 6/2003 | Besson et al. |
| 6,577,897 B1 | 6/2003 | Shurubura et al. |
| 6,579,231 B1 | 6/2003 | Phipps |
| 6,580,942 B1 | 6/2003 | Willshire |
| 6,587,715 B2 | 7/2003 | Singer |
| 6,589,170 B1 | 7/2003 | Flach et al. |
| 6,595,927 B2 | 7/2003 | Pitts-Crick et al. |
| 6,595,929 B2 | 7/2003 | Stivoric et al. |
| 6,600,949 B1 | 7/2003 | Turcott |
| 6,602,201 B1 | 8/2003 | Hepp et al. |
| 6,605,038 B1 | 8/2003 | Teller et al. |
| 6,611,705 B2 | 8/2003 | Hopman et al. |
| 6,616,606 B1 | 9/2003 | Petersen et al. |
| 6,622,042 B1 | 9/2003 | Thacker |
| 6,636,754 B1 | 10/2003 | Baura et al. |
| 6,641,542 B2 | 11/2003 | Cho et al. |
| 6,645,153 B2 | 11/2003 | Kroll et al. |
| 6,649,829 B2 | 11/2003 | Garber et al. |
| 6,650,917 B2 | 11/2003 | Diab et al. |
| 6,658,300 B2 | 12/2003 | Govari et al. |
| 6,659,947 B1 | 12/2003 | Carter et al. |
| 6,659,949 B1 | 12/2003 | Lang et al. |
| 6,687,540 B2 | 2/2004 | Marcovecchio |
| 6,697,658 B2 | 2/2004 | Al-Ali |
| RE38,476 E | 3/2004 | Diab et al. |
| 6,699,200 B2 | 3/2004 | Cao et al. |
| 6,701,271 B2 | 3/2004 | Willner et al. |
| 6,714,813 B2 | 3/2004 | Ishigooka et al. |
| RE38,492 E | 4/2004 | Diab et al. |
| 6,721,594 B2 | 4/2004 | Conley et al. |
| 6,728,572 B2 | 4/2004 | Hsu et al. |
| 6,748,269 B2 | 6/2004 | Thompson et al. |
| 6,749,566 B2 | 6/2004 | Russ |
| 6,751,498 B1 | 6/2004 | Greenberg et al. |
| 6,760,617 B2 | 7/2004 | Ward et al. |
| 6,773,396 B2 | 8/2004 | Flach et al. |
| 6,775,566 B2 | 8/2004 | Nissila |
| 6,790,178 B1 | 9/2004 | Mault et al. |
| 6,795,722 B2 | 9/2004 | Sheraton et al. |
| 6,814,706 B2 | 11/2004 | Barton et al. |
| 6,816,744 B2 | 11/2004 | Garfield et al. |
| 6,821,249 B2 | 11/2004 | Casscells, III et al. |
| 6,824,515 B2 | 11/2004 | Suorsa et al. |
| 6,827,690 B2 | 12/2004 | Bardy |
| 6,829,503 B2 | 12/2004 | Alt |
| 6,858,006 B2 | 2/2005 | MacCarter et al. |
| 6,871,211 B2 | 3/2005 | Labounty et al. |
| 6,878,121 B2 | 4/2005 | Krausman et al. |
| 6,879,850 B2 | 4/2005 | Kimball |
| 6,881,191 B2 | 4/2005 | Oakley et al. |
| 6,887,201 B2 | 5/2005 | Bardy |
| 6,890,096 B2 | 5/2005 | Tokita et al. |
| 6,893,396 B2 | 5/2005 | Schulze et al. |
| 6,894,204 B2 | 5/2005 | Dunshee |
| 6,906,530 B2 | 6/2005 | Geisel |
| 6,912,414 B2 | 6/2005 | Tong |
| 6,936,006 B2 | 8/2005 | Sabra |
| 6,940,403 B2 | 9/2005 | Kail, IV |
| 6,942,622 B1 | 9/2005 | Turcott |
| 6,952,695 B1 | 10/2005 | Trinks et al. |
| 6,970,742 B2 | 11/2005 | Mann et al. |

(56) References Cited

U.S. PATENT DOCUMENTS

| | | |
|---|---|---|
| 6,972,683 B2 | 12/2005 | Lestienne et al. |
| 6,978,177 B1 | 12/2005 | Chen et al. |
| 6,980,851 B2 | 12/2005 | Zhu et al. |
| 6,980,852 B2 | 12/2005 | Jersey-Willuhn et al. |
| 6,985,078 B2 | 1/2006 | Suzuki et al. |
| 6,987,965 B2 | 1/2006 | Ng et al. |
| 6,988,989 B2 | 1/2006 | Weiner et al. |
| 6,993,378 B2 | 1/2006 | Wiederhold et al. |
| 6,997,879 B1 | 2/2006 | Turcott |
| 7,003,346 B2 | 2/2006 | Singer |
| 7,018,338 B2 | 3/2006 | Vetter et al. |
| 7,020,508 B2 | 3/2006 | Stivoric et al. |
| 7,027,862 B2 | 4/2006 | Dahl et al. |
| 7,041,062 B2 | 5/2006 | Friedrichs et al. |
| 7,044,911 B2 | 5/2006 | Drinan et al. |
| 7,047,067 B2 | 5/2006 | Gray et al. |
| 7,050,846 B2 | 5/2006 | Sweeney et al. |
| 7,054,679 B2 | 5/2006 | Hirsh |
| 7,059,767 B2 | 6/2006 | Tokita et al. |
| 7,088,242 B2 | 8/2006 | Aupperle et al. |
| 7,113,826 B2 | 9/2006 | Henry et al. |
| 7,118,531 B2 | 10/2006 | Krill |
| 7,127,370 B2 | 10/2006 | Kelly, Jr. et al. |
| 7,129,836 B2 | 10/2006 | Lawson et al. |
| 7,130,396 B2 | 10/2006 | Rogers et al. |
| 7,130,679 B2 | 10/2006 | Parsonnet et al. |
| 7,133,716 B2 | 11/2006 | Kraemer et al. |
| 7,136,697 B2 | 11/2006 | Singer |
| 7,136,703 B1 | 11/2006 | Cappa et al. |
| 7,142,907 B2 | 11/2006 | Xue et al. |
| 7,149,574 B2 | 12/2006 | Yun et al. |
| 7,149,773 B2 | 12/2006 | Haller et al. |
| 7,153,262 B2 | 12/2006 | Stivoric et al. |
| 7,156,807 B2 | 1/2007 | Carter et al. |
| 7,156,808 B2 | 1/2007 | Quy |
| 7,160,252 B2 | 1/2007 | Cho et al. |
| 7,160,253 B2 | 1/2007 | Nissila |
| 7,166,063 B2 | 1/2007 | Rahman et al. |
| 7,167,743 B2 | 1/2007 | Heruth et al. |
| 7,184,821 B2 | 2/2007 | Belalcazar et al. |
| 7,191,000 B2 | 3/2007 | Zhu et al. |
| 7,194,306 B1 | 3/2007 | Turcott |
| 7,206,630 B1 | 4/2007 | Tarler |
| 7,212,849 B2 | 5/2007 | Zhang et al. |
| 7,215,984 B2 | 5/2007 | Diab et al. |
| 7,215,991 B2 | 5/2007 | Besson et al. |
| 7,238,159 B2 | 7/2007 | Banet et al. |
| 7,248,916 B2 | 7/2007 | Bardy |
| 7,251,524 B1 | 7/2007 | Hepp et al. |
| 7,257,438 B2 | 8/2007 | Kinast |
| 7,261,690 B2 | 8/2007 | Teller et al. |
| 7,277,741 B2 | 10/2007 | Debreczeny et al. |
| 7,284,904 B2 | 10/2007 | Tokita et al. |
| 7,285,090 B2 | 10/2007 | Stivoric et al. |
| 7,294,105 B1 | 11/2007 | Islam |
| 7,295,879 B2 | 11/2007 | Denker et al. |
| 7,297,119 B2 | 11/2007 | Westbrook et al. |
| 7,319,386 B2 | 1/2008 | Collins, Jr. et al. |
| 7,336,187 B2 | 2/2008 | Hubbard, Jr. et al. |
| 7,346,380 B2 | 3/2008 | Axelgaard et al. |
| 7,382,247 B2 | 6/2008 | Welch et al. |
| 7,390,299 B2 | 6/2008 | Weiner et al. |
| 7,395,106 B2 | 7/2008 | Ryu et al. |
| 7,423,526 B2 | 9/2008 | Despotis |
| 7,423,537 B2 | 9/2008 | Bonnet et al. |
| 7,443,302 B2 | 10/2008 | Reeder et al. |
| 7,450,024 B2 | 11/2008 | Wildman et al. |
| 7,468,032 B2 | 12/2008 | Stahmann et al. |
| 2001/0047127 A1 | 11/2001 | New, Jr. et al. |
| 2002/0019586 A1 | 2/2002 | Teller et al. |
| 2002/0019588 A1 | 2/2002 | Marro et al. |
| 2002/0022786 A1 | 2/2002 | Takehara et al. |
| 2002/0028989 A1 | 3/2002 | Pelletier et al. |
| 2002/0032581 A1 | 3/2002 | Reitberg |
| 2002/0045836 A1 | 4/2002 | Alkawwas |
| 2002/0088465 A1 | 7/2002 | Hill |
| 2002/0099277 A1 | 7/2002 | Harry et al. |
| 2002/0116009 A1 | 8/2002 | Fraser et al. |
| 2002/0123672 A1 | 9/2002 | Christophersom et al. |
| 2002/0123674 A1 | 9/2002 | Plicchi et al. |
| 2002/0138017 A1 | 9/2002 | Bui et al. |
| 2002/0167389 A1 | 11/2002 | Uchikoba et al. |
| 2003/0023184 A1 | 1/2003 | Pitts-Crick et al. |
| 2003/0023186 A1 | 1/2003 | Ueda et al. |
| 2003/0028221 A1 | 2/2003 | Zhu et al. |
| 2003/0028327 A1 | 2/2003 | Brunner et al. |
| 2003/0051144 A1 | 3/2003 | Williams |
| 2003/0055460 A1 | 3/2003 | Owen et al. |
| 2003/0083581 A1 | 5/2003 | Taha et al. |
| 2003/0085717 A1 | 5/2003 | Cooper |
| 2003/0087244 A1 | 5/2003 | McCarthy |
| 2003/0092975 A1 | 5/2003 | Casscells, III et al. |
| 2003/0093125 A1 | 5/2003 | Zhu et al. |
| 2003/0093298 A1 | 5/2003 | Hernandez et al. |
| 2003/0100367 A1 | 5/2003 | Cooke |
| 2003/0105411 A1 | 6/2003 | Smallwood et al. |
| 2003/0135127 A1 | 7/2003 | Sackner et al. |
| 2003/0143544 A1 | 7/2003 | McCarthy |
| 2003/0149349 A1 | 8/2003 | Jensen |
| 2003/0187370 A1 | 10/2003 | Kodama |
| 2003/0191503 A1 | 10/2003 | Zhu et al. |
| 2003/0212319 A1 | 11/2003 | Magill |
| 2003/0221687 A1 | 12/2003 | Kaigler |
| 2003/0233129 A1 | 12/2003 | Matos |
| 2004/0006279 A1 | 1/2004 | Arad (Abboud) |
| 2004/0010303 A1 | 1/2004 | Bolea et al. |
| 2004/0015058 A1 | 1/2004 | Besson et al. |
| 2004/0019292 A1 | 1/2004 | Drinan et al. |
| 2004/0044293 A1 | 3/2004 | Burton |
| 2004/0049132 A1 | 3/2004 | Barron et al. |
| 2004/0073094 A1 | 4/2004 | Baker |
| 2004/0073126 A1 | 4/2004 | Rowlandson |
| 2004/0077954 A1 | 4/2004 | Oakley et al. |
| 2004/0100376 A1 | 5/2004 | Lye et al. |
| 2004/0102683 A1 | 5/2004 | Khanuja et al. |
| 2004/0106951 A1 | 6/2004 | Edman et al. |
| 2004/0122489 A1 | 6/2004 | Mazar et al. |
| 2004/0127790 A1 | 7/2004 | Lang et al. |
| 2004/0133079 A1 | 7/2004 | Mazar et al. |
| 2004/0133081 A1 | 7/2004 | Teller et al. |
| 2004/0134496 A1 | 7/2004 | Cho et al. |
| 2004/0143170 A1 | 7/2004 | DuRousseau |
| 2004/0147969 A1 | 7/2004 | Mann et al. |
| 2004/0152956 A1 | 8/2004 | Korman |
| 2004/0158132 A1 | 8/2004 | Zaleski |
| 2004/0167389 A1 | 8/2004 | Brabrand |
| 2004/0167423 A1 | 8/2004 | Pillon et al. |
| 2004/0172080 A1 | 9/2004 | Stadler et al. |
| 2004/0199056 A1 | 10/2004 | Husemann et al. |
| 2004/0215240 A1 | 10/2004 | Lovett et al. |
| 2004/0220639 A1 | 11/2004 | Mulligan et al. |
| 2004/0225199 A1 | 11/2004 | Evanyk et al. |
| 2004/0225203 A1 | 11/2004 | Jemison et al. |
| 2004/0243018 A1 | 12/2004 | Organ et al. |
| 2004/0267142 A1 | 12/2004 | Paul |
| 2005/0015094 A1 | 1/2005 | Keller |
| 2005/0015095 A1 | 1/2005 | Keller |
| 2005/0020935 A1 | 1/2005 | Helzel et al. |
| 2005/0027175 A1 | 2/2005 | Yang |
| 2005/0027204 A1 | 2/2005 | Kligfield et al. |
| 2005/0027207 A1 | 2/2005 | Westbrook et al. |
| 2005/0027918 A1 | 2/2005 | Govindarajulu et al. |
| 2005/0043675 A1 | 2/2005 | Pastore et al. |
| 2005/0054944 A1 | 3/2005 | Nakada et al. |
| 2005/0065445 A1 | 3/2005 | Arzbaecher et al. |
| 2005/0065571 A1 | 3/2005 | Imran |
| 2005/0070768 A1 | 3/2005 | Zhu et al. |
| 2005/0070778 A1 | 3/2005 | Lackey et al. |
| 2005/0080346 A1 | 4/2005 | Gianchandani et al. |
| 2005/0080460 A1 | 4/2005 | Wang et al. |
| 2005/0080463 A1 | 4/2005 | Stahmann et al. |
| 2005/0085734 A1 | 4/2005 | Tehrani |
| 2005/0091338 A1 | 4/2005 | de la Huerga |
| 2005/0096513 A1* | 5/2005 | Ozguz et al. .................. 600/301 |

(56) References Cited

U.S. PATENT DOCUMENTS

| | | |
|---|---|---|
| 2005/0113703 A1 | 5/2005 | Farringdon et al. |
| 2005/0124878 A1 | 6/2005 | Sharony |
| 2005/0124901 A1 | 6/2005 | Misczynski et al. |
| 2005/0124908 A1 | 6/2005 | Belalcazar et al. |
| 2005/0131288 A1 | 6/2005 | Turner et al. |
| 2005/0137464 A1 | 6/2005 | Bomba |
| 2005/0137626 A1 | 6/2005 | Pastore et al. |
| 2005/0148895 A1 | 7/2005 | Misczynski et al. |
| 2005/0158539 A1 | 7/2005 | Murphy et al. |
| 2005/0177038 A1 | 8/2005 | Kolpin et al. |
| 2005/0187482 A1 | 8/2005 | O'Brien et al. |
| 2005/0187796 A1 | 8/2005 | Rosenfeld et al. |
| 2005/0192488 A1 | 9/2005 | Bryenton et al. |
| 2005/0197654 A1 | 9/2005 | Edman et al. |
| 2005/0203433 A1 | 9/2005 | Singer |
| 2005/0203435 A1 | 9/2005 | Nakada |
| 2005/0203436 A1 | 9/2005 | Davies |
| 2005/0203637 A1 | 9/2005 | Edman et al. |
| 2005/0206518 A1 | 9/2005 | Welch et al. |
| 2005/0215914 A1 | 9/2005 | Bornzin et al. |
| 2005/0215918 A1 | 9/2005 | Frantz et al. |
| 2005/0228234 A1 | 10/2005 | Yang |
| 2005/0228244 A1 | 10/2005 | Banet |
| 2005/0239493 A1 | 10/2005 | Batkin et al. |
| 2005/0240087 A1 | 10/2005 | Keenan et al. |
| 2005/0251044 A1 | 11/2005 | Hoctor et al. |
| 2005/0256418 A1 | 11/2005 | Mietus et al. |
| 2005/0261598 A1 | 11/2005 | Banet et al. |
| 2005/0261743 A1 | 11/2005 | Kroll |
| 2005/0267376 A1 | 12/2005 | Marossero et al. |
| 2005/0267377 A1 | 12/2005 | Marossero et al. |
| 2005/0267381 A1 | 12/2005 | Benditt et al. |
| 2005/0273023 A1 | 12/2005 | Bystrom et al. |
| 2005/0277841 A1 | 12/2005 | Shennib |
| 2005/0277842 A1 | 12/2005 | Silva |
| 2005/0277992 A1 | 12/2005 | Koh et al. |
| 2005/0280531 A1 | 12/2005 | Fadem et al. |
| 2005/0283197 A1 | 12/2005 | Daum et al. |
| 2005/0288601 A1 | 12/2005 | Wood et al. |
| 2006/0004300 A1 | 1/2006 | Kennedy |
| 2006/0004377 A1 | 1/2006 | Keller |
| 2006/0009697 A1 | 1/2006 | Banet et al. |
| 2006/0009701 A1 | 1/2006 | Nissila et al. |
| 2006/0010090 A1 | 1/2006 | Brockway et al. |
| 2006/0020218 A1 | 1/2006 | Freeman et al. |
| 2006/0025661 A1 | 2/2006 | Sweeney et al. |
| 2006/0030781 A1 | 2/2006 | Shennib |
| 2006/0030782 A1 | 2/2006 | Shennib |
| 2006/0031102 A1 | 2/2006 | Teller et al. |
| 2006/0041280 A1 | 2/2006 | Stahmann et al. |
| 2006/0047215 A1 | 3/2006 | Newman et al. |
| 2006/0052678 A1 | 3/2006 | Drinan et al. |
| 2006/0058543 A1 | 3/2006 | Walter et al. |
| 2006/0058593 A1 | 3/2006 | Drinan et al. |
| 2006/0064030 A1 | 3/2006 | Cosentino et al. |
| 2006/0064040 A1 | 3/2006 | Berger et al. |
| 2006/0064142 A1 | 3/2006 | Chavan et al. |
| 2006/0066449 A1 | 3/2006 | Johnson |
| 2006/0074283 A1 | 4/2006 | Henderson et al. |
| 2006/0074462 A1 | 4/2006 | Verhoef |
| 2006/0075257 A1 | 4/2006 | Martis et al. |
| 2006/0084881 A1 | 4/2006 | Korzinov et al. |
| 2006/0085049 A1 | 4/2006 | Cory et al. |
| 2006/0089679 A1 | 4/2006 | Zhu et al. |
| 2006/0102476 A1 | 5/2006 | Niwa et al. |
| 2006/0116592 A1 | 6/2006 | Zhou et al. |
| 2006/0122474 A1 | 6/2006 | Teller et al. |
| 2006/0142654 A1 | 6/2006 | Rytky |
| 2006/0142820 A1 | 6/2006 | Von Arx et al. |
| 2006/0149168 A1 | 7/2006 | Czarnek |
| 2006/0155183 A1 | 7/2006 | Kroecker et al. |
| 2006/0155200 A1 | 7/2006 | Ng |
| 2006/0161073 A1 | 7/2006 | Singer |
| 2006/0161205 A1 | 7/2006 | Mitrani et al. |
| 2006/0161459 A9 | 7/2006 | Rosenfeld et al. |
| 2006/0167374 A1 | 7/2006 | Takehara et al. |
| 2006/0173257 A1 | 8/2006 | Nagai et al. |
| 2006/0173269 A1 | 8/2006 | Glossop |
| 2006/0195020 A1 | 8/2006 | Martin et al. |
| 2006/0195039 A1 | 8/2006 | Drew et al. |
| 2006/0195097 A1 | 8/2006 | Evans et al. |
| 2006/0195144 A1 | 8/2006 | Giftakis et al. |
| 2006/0202816 A1 | 9/2006 | Crump et al. |
| 2006/0212097 A1 | 9/2006 | Varadan et al. |
| 2006/0224051 A1 | 10/2006 | Teller et al. |
| 2006/0224072 A1 | 10/2006 | Shennib |
| 2006/0224079 A1 | 10/2006 | Washchuk |
| 2006/0235281 A1 | 10/2006 | Tuccillo |
| 2006/0235316 A1 | 10/2006 | Ungless et al. |
| 2006/0235489 A1 | 10/2006 | Drew et al. |
| 2006/0241641 A1 | 10/2006 | Albans et al. |
| 2006/0241701 A1 | 10/2006 | Markowitz et al. |
| 2006/0241722 A1 | 10/2006 | Thacker et al. |
| 2006/0247545 A1 | 11/2006 | St. Martin |
| 2006/0252999 A1 | 11/2006 | Devaul et al. |
| 2006/0253005 A1 | 11/2006 | Drinan et al. |
| 2006/0253044 A1 | 11/2006 | Zhang et al. |
| 2006/0258952 A1 | 11/2006 | Stahmann et al. |
| 2006/0264730 A1 | 11/2006 | Stivoric et al. |
| 2006/0264767 A1 | 11/2006 | Shennib |
| 2006/0264776 A1 | 11/2006 | Stahmann et al. |
| 2006/0271116 A1 | 11/2006 | Stahmann et al. |
| 2006/0276714 A1 | 12/2006 | Holt et al. |
| 2006/0281981 A1 | 12/2006 | Jang et al. |
| 2006/0281996 A1 | 12/2006 | Kuo et al. |
| 2006/0293571 A1 | 12/2006 | Bao et al. |
| 2006/0293609 A1 | 12/2006 | Stahmann et al. |
| 2007/0010721 A1 | 1/2007 | Chen et al. |
| 2007/0010750 A1 | 1/2007 | Ueno et al. |
| 2007/0015973 A1 | 1/2007 | Nanikashvili |
| 2007/0015976 A1 | 1/2007 | Miesel et al. |
| 2007/0016089 A1 | 1/2007 | Fischell et al. |
| 2007/0021678 A1 | 1/2007 | Beck et al. |
| 2007/0021790 A1 | 1/2007 | Kieval et al. |
| 2007/0021792 A1 | 1/2007 | Kieval et al. |
| 2007/0021794 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0027388 A1 | 2/2007 | Chou |
| 2007/0027497 A1 | 2/2007 | Parnis |
| 2007/0038038 A1 | 2/2007 | Stivoric et al. |
| 2007/0038078 A1 | 2/2007 | Osadchy |
| 2007/0038255 A1 | 2/2007 | Kieval et al. |
| 2007/0038262 A1 | 2/2007 | Kieval et al. |
| 2007/0043301 A1 | 2/2007 | Martinsen et al. |
| 2007/0043303 A1 | 2/2007 | Osypka et al. |
| 2007/0048224 A1 | 3/2007 | Howell et al. |
| 2007/0060800 A1 | 3/2007 | Drinan et al. |
| 2007/0060802 A1 | 3/2007 | Ghevondian et al. |
| 2007/0069887 A1 | 3/2007 | Welch et al. |
| 2007/0073132 A1 | 3/2007 | Vosch |
| 2007/0073168 A1 | 3/2007 | Zhang et al. |
| 2007/0073181 A1 | 3/2007 | Pu et al. |
| 2007/0073361 A1 | 3/2007 | Goren et al. |
| 2007/0082189 A1 | 4/2007 | Gillette |
| 2007/0083092 A1 | 4/2007 | Rippo et al. |
| 2007/0092862 A1 | 4/2007 | Gerber |
| 2007/0104840 A1 | 5/2007 | Singer |
| 2007/0106132 A1 | 5/2007 | Elhag et al. |
| 2007/0106137 A1 | 5/2007 | Baker, Jr. et al. |
| 2007/0106167 A1 | 5/2007 | Kinast |
| 2007/0118039 A1 | 5/2007 | Bodecker et al. |
| 2007/0123756 A1 | 5/2007 | Kitajima et al. |
| 2007/0123903 A1 | 5/2007 | Raymond et al. |
| 2007/0123904 A1 | 5/2007 | Stad et al. |
| 2007/0129622 A1 | 6/2007 | Bourget et al. |
| 2007/0129643 A1* | 6/2007 | Kwok et al. .................. 600/529 |
| 2007/0129769 A1 | 6/2007 | Bourget et al. |
| 2007/0142715 A1 | 6/2007 | Banet et al. |
| 2007/0142732 A1 | 6/2007 | Brockway et al. |
| 2007/0149282 A1 | 6/2007 | Lu et al. |
| 2007/0150008 A1 | 6/2007 | Jones et al. |

(56) References Cited

U.S. PATENT DOCUMENTS

| | | |
|---|---|---|
| 2007/0150009 A1 | 6/2007 | Kveen et al. |
| 2007/0150029 A1 | 6/2007 | Bourget et al. |
| 2007/0162089 A1 | 7/2007 | Mosesov |
| 2007/0167753 A1 | 7/2007 | Van Wyk et al. |
| 2007/0167848 A1 | 7/2007 | Kuo et al. |
| 2007/0167849 A1 | 7/2007 | Zhang et al. |
| 2007/0167850 A1 | 7/2007 | Russell et al. |
| 2007/0172424 A1 | 7/2007 | Roser |
| 2007/0173705 A1 | 7/2007 | Teller et al. |
| 2007/0180047 A1 | 8/2007 | Dong et al. |
| 2007/0180140 A1 | 8/2007 | Welch et al. |
| 2007/0191723 A1 | 8/2007 | Prystowsky et al. |
| 2007/0207858 A1 | 9/2007 | Breving |
| 2007/0208233 A1 | 9/2007 | Kovacs |
| 2007/0208235 A1 | 9/2007 | Besson et al. |
| 2007/0208262 A1 | 9/2007 | Kovacs |
| 2007/0232867 A1 | 10/2007 | Hansmann |
| 2007/0249946 A1 | 10/2007 | Kumar et al. |
| 2007/0250121 A1 | 10/2007 | Miesel et al. |
| 2007/0255120 A1 | 11/2007 | Rosnov |
| 2007/0255153 A1 | 11/2007 | Kumar et al. |
| 2007/0255184 A1 | 11/2007 | Shennib |
| 2007/0255531 A1 | 11/2007 | Drew |
| 2007/0260133 A1 | 11/2007 | Meyer |
| 2007/0260155 A1 | 11/2007 | Rapoport et al. |
| 2007/0260289 A1 | 11/2007 | Giftakis et al. |
| 2007/0270707 A1 | 11/2007 | Belalcazar |
| 2007/0276273 A1 | 11/2007 | Watson, Jr. |
| 2007/0282173 A1 | 12/2007 | Wang et al. |
| 2007/0299325 A1 | 12/2007 | Farrell et al. |
| 2008/0004499 A1 | 1/2008 | Davis |
| 2008/0004904 A1 | 1/2008 | Tran |
| 2008/0024293 A1 | 1/2008 | Stylos |
| 2008/0024294 A1 | 1/2008 | Mazar |
| 2008/0039700 A1 | 2/2008 | Drinan et al. |
| 2008/0058614 A1 | 3/2008 | Banet et al. |
| 2008/0059239 A1 | 3/2008 | Gerst et al. |
| 2008/0091089 A1 | 4/2008 | Guillory et al. |
| 2008/0114220 A1 | 5/2008 | Banet et al. |
| 2008/0139934 A1 | 6/2008 | McMorrow et al. |
| 2008/0146892 A1 | 6/2008 | LeBoeuf et al. |
| 2008/0167538 A1 | 7/2008 | Teller et al. |
| 2008/0171918 A1 | 7/2008 | Teller et al. |
| 2008/0171922 A1 | 7/2008 | Teller et al. |
| 2008/0171929 A1 | 7/2008 | Katims |
| 2008/0183052 A1 | 7/2008 | Teller et al. |
| 2008/0200774 A1 | 8/2008 | Luo |
| 2008/0214903 A1 | 9/2008 | Orbach |
| 2008/0221399 A1 | 9/2008 | Zhou et al. |
| 2008/0221402 A1 | 9/2008 | Despotis |
| 2008/0224852 A1 | 9/2008 | Dicks et al. |
| 2008/0228084 A1 | 9/2008 | Bedard et al. |
| 2008/0234594 A1* | 9/2008 | Brooks et al. .................. 600/513 |
| 2008/0287751 A1 | 11/2008 | Stivoric et al. |
| 2008/0287752 A1 | 11/2008 | Stroetz et al. |
| 2008/0294019 A1 | 11/2008 | Tran |
| 2008/0294020 A1 | 11/2008 | Sapounas |
| 2008/0318681 A1 | 12/2008 | Rofougaran et al. |
| 2008/0319279 A1 | 12/2008 | Ramsay et al. |
| 2009/0005016 A1 | 1/2009 | Eng et al. |
| 2009/0018410 A1 | 1/2009 | Coene et al. |
| 2009/0054737 A1 | 2/2009 | Magar et al. |
| 2009/0062670 A1 | 3/2009 | Sterling et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1* | 3/2009 | Libbus et al. .................. 600/301 |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076401 A1 | 3/2009 | Mazar et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0171236 A1* | 7/2009 | Davies .......................... 600/547 |
| 2009/0182204 A1 | 7/2009 | Semler et al. |
| 2009/0234410 A1 | 9/2009 | Libbus et al. |
| 2009/0264792 A1 | 10/2009 | Mazar |
| 2009/0292194 A1 | 11/2009 | Libbus et al. |
| 2010/0056881 A1 | 3/2010 | Libbus et al. |
| 2010/0191310 A1 | 7/2010 | Bly et al. |

FOREIGN PATENT DOCUMENTS

| | | |
|---|---|---|
| WO | WO 02/092101 A1 | 11/2002 |
| WO | WO 03/082080 A2 | 10/2003 |
| WO | WO 2005/051164 A2 | 6/2005 |
| WO | WO 2005/104930 A1 | 11/2005 |
| WO | 2005/122888 A1 | 12/2005 |
| WO | WO 2006/008745 A2 | 1/2006 |
| WO | WO 2006/102476 A2 | 9/2006 |
| WO | WO 2006/111878 A1 | 11/2006 |
| WO | WO 2007/041783 A1 | 4/2007 |
| WO | WO 2007/106455 A2 | 9/2007 |

OTHER PUBLICATIONS

3M Corporation, "3M Surgical Tapes—Choose the Correct Tape" quicksheet (2004).

Abraham, "New approaches to monitoring heart failure before symptoms appear," Rev Cardiovasc Med. 2006 ;7 Suppl 1 :33-41.

AD5934: 250 kSPS 12-Bit Impedance Converter Network Analyzer, Analog Devices, Rev. A. Retrieved from the Internet: <<http://www.analog.com/static/imported-files/data_sheets/AD5934.pdf>>, 40 pages. Copyright 2005-2008.

Adams, Jr. "Guiding heart failure care by invasive hemodynamic measurements: possible or useful?", Journal of Cardiac Failure 2002; 8(2):71-73.

Adamson et al., "Continuous autonomic assessment in patients with symptomatic heart failure: prognostic value of heart rate variability measured by an implanted cardiac resynchronization device ," Circulation. 2004;110:2389-2394.

Adamson et al., "Ongoing right ventricular hemodynamics in heart failure," J Am Coll Cardiol, 2003; 41:565-57.

Adamson, "Integrating device monitoring into the infrastructure and workflow of routine practice," Rev Cardiovasc Med. 2006 ;7 Suppl 1:42-6.

Adhere [presentation], "Insights from the ADHERE Registry: Data from over 100,000 patient cases," 2005, 70 pages total.

Advamed White Sheet, "Health Information Technology: Improving Patient Safety and Quality of Care," Jun. 2005, 23 pages.

Aghababian, "Acutely decompensated heart failure: opportunities to improve care and outcomes in the emergency department," Rev Cardiovasc Med. 2002;3 Suppl 4:S3-9.

Albert, "Bioimpedance to prevent heart failure hospitalization," Curr Heart Fail Rep. Sep. 2006;3(3):136-42.

American Heart Association, "Heart Disease and Stroke Statistics—2006 Update," 2006, 43 pages.

American Heart Association, "Heart Disease and Stroke Statistics—2007 Update. A Report From the American Heart Association Statistics Committee and Stroke Statistics Subcommittee," Circulation 2007; 115;e69-e171.

Belalcazar et al., "Monitoring lung edema using the pacemaker pulse and skin electrodes," Physiol. Meas. 2005; 26:S153-S163.

Bennet, "Development of implantable devices for continuous ambulatory monitoring of central hemodynamic values in heart failure patients," PACE Jun. 2005; 28:573-584.

Bourge, "Case studies in advanced monitoring with the chronicle device," Rev Cardiovasc Med. 2006 ;7 Suppl 1:S56-61.

Braunschweig, "Continous haemodynamic monitoring during withdrawal of diuretics in patients with congestive heart failure," European Heart Journal 2002 23(1):59-69.

(56) References Cited

OTHER PUBLICATIONS

Braunschweig, "Dynamic changes in right ventricular pressures during haemodialysis recorded with an implantable haemodynamic monitor ," Nephrol Dial Transplant 2006; 21:176-183.
Brennan, "Measuring a Grounded Impedance Profile Using the AD5933," Analog Devices, 2006; retrieved from the internet <<http://http://www.analog.com/static/imported-files/application_notes/427095282381510189AN847_0.pdf>>, 12 pages total.
Buono et al., "The effect of ambient air temperature on whole-body bioelectrical impedance," Physiol. Meas. 2004;25:119-123.
Burkhoff et al., "Heart failure with a normal ejection fraction: Is it really a disorder of diastolic function?" Circulation 2003; 107:656-658.
Burr et al., "Heart rate variability and 24-hour minimum heart rate," Biological Research for Nursing, 2006; 7(4):256-267.
Cardionet, "CardioNet Mobile Cardiac Outpatient Telemetry: Addendum to Patient Education Guide", CardioNet, Inc., 2007, 2 pages.
Cardionet, "Patient Education Guide", CardioNet, Inc., 2007, 7 pages.
Charach et al., "Transthoracic monitoring of the impedance of the right lung in patients with cardiogenic pulmonary edema," Crit Care Med Jun. 2001;29(6):1137-1144.
Charlson et al., "Can disease management target patients most likely to generate high costs? The Impact of Comorbidity," Journal of General Internal Medicine, Apr. 2007, 22(4):464-469.
Chaudhry et al., "Telemonitoring for patients with chronic heart failure: a systematic review," J Card Fail. Feb. 2007; 13(1): 56-62.
Chung et al., "White coat hypertension: Not so benign after all?," Journal of Human Hypertension (2003) 17, 807-809.
Cleland et al., "The EuroHeart Failure survey programme—a survey on the quality of care among patients with heart failure in Europe—Part 1: patient characteristics and diagnosis," European Heart Journal 2003 24(5):442-463.
Cooley, "The Parameters of Transthoracic Electical Conduction," Annals of the New York Academy of Sciences, 1970; 170(2):702-713.
Cowie et al., "Hospitalization of patients with heart failure. A population-based study," European Heart Journal 2002 23(11):877-885.
Dimri, Chapter 1: Fractals in geophysics and seimology: an introduction, Fractal Behaviour of the Earth System, Springer Berlin Heidelberg 2005, pp. 1-22. [Summary and 1st page Only].
El-Dawlatly et al., "Impedance cardiography: noninvasive assessment of hemodynamics and thoracic fluid content during bariatric surgery," Obesity Surgery, May 2005, 15(5):655-658.
EM Microelectronic -Marin SA, "Plastic Flexible LCD," [product brochure]; retrieved from the Internet: <<http://www.em-microelectronic.com/Line.asp?IdLine=48>>, copyright 2009, 2 pages total.
Erdmann, "Editorials: The value of diuretics in chronic heart failure demonstrated by an implanted haemodynamic monitor," European Heart Journal 2002 23(1):7-9.
FDA—Medtronic Chronicle Implantable Hemodynamic Monitoring System P050032: Panel Package Section 11: Chronicle IHM Summary of Safety and Effectiveness, 2007; retrieved from the Internet: <http://www.fda.gov/OHRMS/DOCKETS/AC/07/briefing/2007-4284b1_04.pdf>, 77 pages total.
FDA—Medtronic Inc., Chronicle 9520B Implantable Hemodynamic Monitor Reference Manual, 2007, 112 pages.
FDA Executive Summary Memorandum, prepared for Mar. 1, 2007 meeting of the Circulatory Systems Devices Advisory Panel, P050032 Medtronic, Inc. Chronicle Implantable Hemodynamic Monitor (IHM) System, 23 pages. Retrieved from the Internet: <<http://www.fda.gov/ohrms/dockets/ac/07/briefing/2007-4284b1_02.pdf>>.
FDA Executive Summary, Medtronic Chronicle Implantable Hemodynamic Monitoring System P050032: Panel Package Sponsor Executive Summary; vol. 1, section 4: Executive Summary. 2007, 12 pages total. Retrieved from the Internet: <<http://www.fda.gov/OHRMS/DOCKETS/AC/07/briefing/2007-4284b1_03.pdf>>.
FDA, Draft questions for Chronicle Advisory Panel Meeting, 2007, 3 pages total. Retrieved from the Internet: <<http://www.fda.gov/ohrms/dockets/ac/07/questions/2007-4284q1_draft.pdf>>.
FDA, References for Mar. 1 Circulatory System Devices Panel, 2007, 1 page total. Retrieved from the Internet: <<http://www.fda.gov/OHRMS/DOCKETS/AC/07/briefing/2007-4284bib1_01.pdf>>.
Fonarow et al., "Risk stratification for in-hospital mortality in acutely decompensated heart failure: classification and regression tree analysis," JAMA. Feb. 2, 2005;293(5):572-580.
Fonarow, "How well are chronic heart failure patients being managed?", Rev Cardiovasc Med. 2006;7 Suppl 1:S3-11.
Fonarow, "Proactive monitoring and management of the chronic heart failure patient," Rev Cardiovasc Med. 2006; 7 Suppl 1:S1-2.
Fonarow, "The Acute Decompensated Heart Failure National Registry (ADHERE): opportunities to improve care of patients hospitalized with acute decompensated heart failure," Rev Cardiovasc Med. 2003;4 Suppl 7:S21-S30.
Ganion et al., "Intrathoracic impedance to monitor heart failure status: a comparison of two methods in a chronic heart failure dog model," Congest Heart Fail. Jul.-Aug. 2005;11(4):177-81, 211.
Gass et al., "Critical pathways in the management of acute decompensated heart failure: A CME-Accredited monograph," Mount Sinai School of Medicine, 2004, 32 pages total.
Gheorghiade et al., "Congestion is an important diagnostic and therapeutic target in heart failure," Rev Cardiovasc Med. 2006 ;7 Suppl 1 :12-24.
Gilliam, III et al., "Changes in heart rate variability, quality of life, and activity in cardiac resynchronization therapy patients: results of the HF-HRV registry," Pacing and Clinical Electrophysiology, Jan. 18, 2007; 30(1): 56-64.
Gilliam, III et al., "Prognostic value of heart rate variability footprint and standard deviation of average 5-minute intrinsic R-R intervals for mortality in cardiac resynchronization therapy patients," J Electrocardiol. Oct. 2007;40(4):336-42.
Gniadecka, "Localization of dermal edema in lipodermatosclerosis, lymphedema, and cardiac insufficiency high-frequency ultrasound examination of intradermal echogenicity," J Am Acad oDermatol, Jul. 1996; 35(1):37-41.
Goldberg et al., "Randomized trial of a daily electronic home monitoring system in patients with advanced heart failure: The Weight Monitoring in Heart Failure (WHARF) Trial," American Heart Journal, Oct. 2003; 416(4):705-712.
Grap et al., "Actigraphy in the Critically Ill: Correlation With Activity, Agitation, and Sedation," American Journal of Critical Care. 2005;14: 52-60.
Gudivaka et al., "Single- and multifrequency models for bioelectrical impedance analysis of body water compartments," J Appl Physiol, 1999;87(3):1087-1096.
Guyton et al., Unit V: The Body Fluids and Kidneys, Chapter 25: The Body Fluid Compartments: Extracellular and Intracellular Fluids; Interstitial Fluid and Edema, Guyton & Hall Textbook of Medical Physiology 11th Edition, Saunders 2005; pp. 291-306.
Hadase et al., "Very low frequency power of heart rate variability is a powerful predictor of clinical prognosis in patients with congestive heart Failure," Circ J 2004; 68(4):343-347.
Hallstrom et al., "Structural relationships between measures based on heart beat intervals: potential for improved risk assessment," IEEE Biomedical Engineering 2004, 51(8):1414-1420.
HFSA 2006 Comprehensive Heart Failure Practice Guideline—Executive Summary: HFSA 2006 Comprehensive Heart Failure Practice Guideline, Journal of Cardiac Failure 2006;12(1):10-e38.
HFSA 2006 Comprehensive Heart Failure Practice Guideline—Section 12: Evaluation and Management of Patients With Acute Decompensated Heart Failure, Journal of Cardiac Failure 2006;12(1):e86-e103.
HFSA 2006 Comprehensive Heart Failure Practice Guideline—Section 2: Conceptualization and Working Definition of Heart Failure, Journal of Cardiac Failure 2006;12(1):e10-e11.
HFSA 2006 Comprehensive Heart Failure Practice Guideline—Section 3: Prevention of Ventricular Remodeling Cardiac Dysfunction, and Heart Failure Overview, Journal of Cardiac Failure 2006;12(1):e12-e15.

(56) References Cited

OTHER PUBLICATIONS

HFSA 2006 Comprehensive Heart Failure Practice Guideline—Section 4: Evaluation of Patients for Ventricular Dysfunction and Heart Failure, Journal of Cardiac Failure 2006;12(1):e16-e25.
HFSA 2006 Comprehensive Heart Failure Practice Guideline—Section 8: Disease Management in Heart Failure Education and Counseling, Journal of Cardiac Failure 2006;12(1):e58-e68.
HRV Enterprises, LLC, "Heart Rate Variability Seminars," downloaded from the Internet: <<http://hrventerprise.com/>>on Apr. 24, 2008, 3 pages total.
HRV Enterprises, LLC, "LoggerPro HRV Biosignal Analysis," downloaded from the Internet: <<http://hrventerprise.com/products.html on Apr. 24, 2008, 3 pages total.
Hunt et al., "ACC/AHA 2005 Guideline Update for the Diagnosis and Management of Chronic Heart Failure in the Adult: A Report of the American College of Cardiology/American Heart Association Task Force on Practice Guidelines (Writing Committee to Update the 2001 Guidelines for the Evaluation and Management of Heart Failure): Developed in Collaboration With the American College of Chest Physicians and the International Society for Heart and Lung Transplantation: Endorsed by the Heart Rhythm Society," Circulation. 2005;112:e154-e235.
Hunt et al., ACC/AHA Guidelines for the Evaluation and Management of Chronic Heart Failure in the Adult: Executive Summary A Report of the American College of Cardiology/American Heart Association Task Force on Practice Guidelines (Committee to Revise the 1995 Guidelines for the Evaluation and Management of Heart Failure), Circulation. 2001;104:2996-3007.
Imhoff et al., "Noninvasive whole-body electrical bioimpedance cardiac output and invasive thermodilution cardiac output in high-risk surgical patients," Critical Care Medicine 2000; 28(8):2812-2818.
Jaeger et al., "Evidence for Increased Intrathoracic Fluid Volume in Man at High Altitude," J Appl Physiol 1979; 47(6): 670-676.
Jaio et al., "Variance fractal dimension analysis of seismic refraction signals," WESCANEX 97: Communications, Power and Computing. IEEE Conference Proceedings., May 22-23, 1997, pp. 163-167 [Abstract Only].
Jerant et al., "Reducing the cost of frequent hospital admissions for congestive heart failure: a randomized trial of a home telecare intervention," Medical Care 2001, 39(11):1234-1245.
Kasper et al., "A randomized trial of the efficacy of multidisciplinary care in heart failure outpatients at high risk of hospital readmission," J Am Coll Cardiol, 2002; 39:471-480.
Kaukinen, "Cardiac output measurement after coronary artery bypass grafting using bolus thermodilution, continuous thermodilution, and whole-body impedance cardiography," Journal of Cardiothoracic and Vascular Anesthesia 2003; 17(2):199-203.
Kawaguchi et al., "Combined ventricular systolic and arterial stiffening in patients with heart failure and preserved ejection fraction: implications for systolic and diastolic reserve limitations," Circulation. 2003;107:714-720.
Kawasaki et al., "Heart rate turbulence and clinical prognosis in hypertrophic cardiomyopathy and myocardial infarction," Circ J. Jul. 2003;67(7):601-604.
Kearney et al., "Predicting death due to progressive heart failure in patients with mild-to-moderate chronic heart failure," J Am Coll Cardiol, 2002; 40(10):1801-1808.
Kitzman et al., "Pathophysiological characterization of isolated diastolic heart failure in comparison to systolic heart failure," JAMA Nov. 2002; 288(17):2144-2150.
Kööbi et al., "Non-invasive measurement of cardiac output: whole-body impedance cardiography in simultaneous comparison with thermodilution and direct oxygen Fick methods," Intensive Care Medicine 1997; 23(11):1132-1137.
Koyama et al., "Evaluation of heart-rate turbulence as a new prognostic marker in patients with chronic heart failure," Circ J 2002; 66(10):902-907.
Krumholz et al., "Predictors of readmission among elderly survivors of admission with heart failure," American Heart Journal 2000; 139(1):72-77.

Kyle et al., "Bioelectrical Impedance Analysis—part I: review of principles and methods," Clin Nutr. Oct. 2004; 23(5):1226-1243.
Kyle et al., "Bioelectrical Impedance Analysis—part II: utilization in clinical practice," Clin Nutr. Oct. 2004; 23(5):1430-1453.
Lee et al., "Predicting mortality among patients hospitalized for heart failure: derivation and validation of a clinical model," JAMA 2003;290(19):2581-2587.
Leier "The Physical Examination in Heart Failure—Part I," Congest Heart Fail. Jan.-Feb. 2007;13(1):41-47.
Liu et al., "Fractal analysis with applications to seismological pattern recognition of underground nuclear explosions," Singal Processing, Sep. 2000, 80(9):1849-1861. [Abstract Only].
Lozano-Nieto, "Impedance ratio in bioelectrical impedance measurements for body fluid shift determination," Proceedings of the IEEE 24th Annual Northeast Bioengineering Conference, Apr. 9-10, 1998, pp. 24-25.
Lucreziotti et al., "Five-minute recording of heart rate variability in severe chronic heart failure : Correlates with right ventricular function and prognostic implications," American Heart Journal 2000; 139(6):1088-1095.
Lüthje et al., "Detection of heart failure decompensation using intrathoracic impedance monitoring by a triple-chamber implantable defibrillator," Heart Rhythm Sep. 2005;2(9):997-999.
Magalski et al., "Continuous ambulatory right heart pressure measurements with an implantable hemodynamic monitor: a multicenter, 12-Month Follow-up Study of Patients With Chronic Heart Failure," J Card Fail 2002, 8(2):63-70.
Mahlberg et al., "Actigraphy in agitated patients with dementia: Monitoring treatment outcomes," Zeitschrift für Gerontologie und Geriatrie, Jun. 2007; 40(3)178-184. [Abstract Only].
Matthie et al., "Analytic assessment of the various bioimpedance methods used to estimate body water," Appl Physiol 1998; 84(5):1801-1816.
Matthie, "Second generation mixture theory equation for estimating intracellular water using bioimpedance spectroscopy," J Appl Physiol 2005; 99:780-781.
McMurray et al., "Heart Failure: Epidemiology, Aetiology, and Prognosis of Heart Failure," Heart 2000;83:596-602.
Miller, "Home monitoring for congestive heart failure patients," Caring Magazine, Aug. 1995: 53-54.
Moser et al., "Improving outcomes in heart failure: it's not unusual beyond usual Care," Circulation. 2002;105:2810-2812.
Nagels et al., "Actigraphic measurement of agitated behaviour in dementia," International journal of geriatric psychiatry , 2009; 21(4):388-393. [Abstract Only].
Nakamura et al., "Universal scaling law in human behavioral organization," Physical Review Letters, Sep. 28, 2007; 99(13):138103 (4 pages).
Nakaya, "Fractal properties of seismicity in regions affected by large, shallow earthquakes in western Japan: Implications for fault formation processes based on a binary fractal fracture network model," Journal of geophysical research, Jan. 2005; 11(B1):B01310.1-B01310.15. [Abstract Only].
Naylor et al., "Comprehensive discharge planning for the hospitalized elderly: a randomized clinical trial," Amer. College Physicians 1994; 120(12):999-1006.
Nieminen et al., "EuroHeart Failure Survey II (EHFS II): a survey on hospitalized acute heart failure patients: description of population," European Heart Journal 2006; 27(22):2725-2736.
Nijsen et al., "The potential value of three-dimensional accelerometry for detection of motor seizures in severe epilepsy," Epilepsy Behav. Aug. 2005;7(1):74-84.
Noble et al., "Diuretic induced change in lung water assessed by electrical impedance tomography," Physiol. Meas. 2000; 21(1):155-163.
Noble et al., "Monitoring patients with left ventricular failure by electrical impedance tomography," Eur J Heart Fail. Dec. 1999;1(4):379-84.
O'Connell et al., "Economic impact of heart failure in the United States: time for a different approach," J Heart Lung Transplant., Jul.-Aug. 1994 ; 13(4):S107-S112.

(56) References Cited

OTHER PUBLICATIONS

Ohlsson et al., "Central hemodynamic responses during serial exercise tests in heart failure patients using implantable hemodynamic monitors," Eur J Heart Fail. Jun. 2003;5(3):253-259.
Ohlsson et al., "Continuous ambulatory monitoring of absolute right ventricular pressure and mixed venous oxygen saturation in patients with heart failure using an implantable haemodynamic monitor," European Heart Journal 2001 22(11):942-954.
Packer et al., "Utility of impedance cardiography for the identification of short-term risk of clinical decompensation in stable patients with chronic heart failure," J Am Coll Cardiol, 2006; 47(11):2245-2252.
Palatini et al., "Predictive value of clinic and ambulatory heart rate for mortality in elderly subjects with systolic hypertension" Arch Intern Med. 2002;162:2313-2321.
Piiria et al., "Crackles in patients with fibrosing alveolitis bronchiectasis, COPD, and Heart Failure," Chest May 1991; 99(5):1076-1083.
Pocock et al., "Predictors of mortality in patients with chronic heart failure," Eur Heart J 2006; (27): 65-75.
Poole-Wilson, "Importance of control of fluid volumes in heart failure," European Heart Journal 2000; 22(11):893-894.
Raj et al., 'Letter Regarding Article by Adamson et al, "Continuous Autonomic Assessment in Patients With Symptomatic Heart Failure: Prognostic Value of Heart Rate Variability Measured by an Implanted Cardiac Resynchronization Device"', Circulation 2005;112:e37-e38.
Ramirez et al., "Prognostic value of hemodynamic findings from impedance cardiography in hypertensive stroke," AJH 2005; 18(20):65-72.
Rich et al., "A multidisciplinary intervention to prevent the readmission of elderly patients with congestive heart failure," New Engl. J. Med. 1995;333:1190-1195.
Roglieri et al., "Disease management interventions to improve outcomes in congestive heart failure," Am J Manag Care. Dec. 1997;3(12):1831-1839.
Sahalos et al., "The Electrical impedance of the human thorax as a guide in evaluation of intrathoracic fluid volume," Phys. Med. Biol. 1986; 31:425-439.
Saxon et al., "Remote active monitoring in patients with heart failure (rapid-rf): design and rationale," Journal of Cardiac Failure 2007; 13(4):241-246.
Scharf et al., "Direct digital capture of pulse oximetry waveforms," Proceedings of the Twelfth Southern Biomedical Engineering Conference, 1993., pp. 230-232.
Shabetai, "Monitoring heart failure hemodynamics with an implanted device: its potential to improve outcome," J Am Coll Cardiol, 2003; 41:572-573.
Small, "Integrating monitoring into the Infrastructure and Workflow of Routine Practice: OptiVol," Rev Cardiovasc Med. 2006 ;7 Supp 1: S47-S55.
Smith et al., "Outcomes in heart failure patients with preserved ejection fraction: mortality, readmission, and functional decline ," J Am Coll Cardiol, 2003; 41:1510-1518.
Something in the way he moves, The Economist, 2007, retrieved from the Internet: http://www.economist.com/science/printerFriendly.cfm?story id=9861412>>.
Starling, "Improving care of chronic heart failure: advances from drugs to devices," Cleveland Clinic Journal of Medicine Feb. 2003; 70(2):141-146.
Steijaert et al., "The use of multi-frequency impedance to determine total body water and extracellular water in obese and lean female individuals," International Journal of Obesity Oct. 1997; 21(10):930-934.
Stewart et al., "Effects of a home-based intervention among patients with congestive heart failure discharged from acute hospital care," Arch Intern Med. 1998;158:1067-1072.
Stewart et al., "Effects of a multidisciplinary, home-based intervention on planned readmissions and survival among patients with chronic congestive heart failure: a randomised controlled study," The Lancet Sep. 1999, 354(9184):1077-1083.
Stewart et al., "Home-based intervention in congestive heart failure: long-term implications on readmission and survival," Circulation. 2002;105:2861-2866.
Stewart et al., "Prolonged beneficial effects of a home-based intervention on unplanned readmissions and mortality among patients with congestive heart failure," Arch Intern Med. 1999;159:257-261.
Stewart et al., "Trends in Hospitalization for Heart Failure in Scotland, 1990-1996. An Epidemic that has Reached Its Peak?," European Heart Journal 2001 22(3):209-217.
Swedberg et al., "Guidelines for the diagnosis and treatment of chronic heart failure: executive summary (update 2005): The Task Force for the Diagnosis and Treatment of Chronic Heart Failure of the European Society of Cardiology," Eur Heart J. Jun. 2005; 26(11):1115-1140.
Tang, "Case studies in advanced monitoring: OptiVol," Rev Cardiovasc Med. 2006;7 Suppl 1:S62-S66.
The ESCAPE Investigators and ESCAPE Study Coordinators, "Evaluation Study of Congestive Heart Failure and Pulmonary Artery Catheterization Effectiveness," JAMA 2005;294:1625-1633.
Tosi et al., "Seismic signal detection by fractal dimension analysis ," Bulletin of the Seismological Society of America; Aug. 1999; 89(4):970-977. [Abstract Only].
Van De Water et al., "Monitoring the chest with impedance," Chest. 1973;64:597-603.
Van Someren, "Actigraphic monitoring of movement and rest-activity rhythms inaging, Alzheimer's disease, and Parkinson's disease," IEEE Transactions on Rehabilitation Engineering, Dec. 1997; 5(4):394-398. [Abstract Only].
Vasan et al., "Congestive heart failure in subjects with normal versus reduced left ventricular ejection fraction," J Am Coll Cardiol, 1999; 33:1948-1955.
Verdecchia et al., "Adverse prognostic value of a blunted circadian rhythm of heart rate in essential hypertension," Journal of Hypertension 1998; 16(9):1335-1343.
Verdecchia et al., "Ambulatory pulse pressure: a potent predictor of total cardiovascular risk in hypertension," Hypertension. 1998;32:983-988.
Vollmann et al., "Clinical utility of intrathoracic impedance monitoring to alert patients with an implanted device of deteriorating chronic heart failure," Euorpean Heart Journal Advance Access published on Feb. 19, 2007, downloaded from the Internet:<<http://eurheartj.oxfordjournals.org/cgi/content/full/ehl506v1>>, 6 pages total.
Vuksanovic et al., "Effect of posture on heart rate variability spectral measures in children and young adults with heart disease," International Journal of Cardiology 2005;101(2): 273-278.
Wang et al., "Feasibility of using an implantable system to measure thoracic congestion in an ambulatory chronic heart failure canine model," PACE 2005;28(5):404-411.
Wickemeyer et al., #197—"Association between atrial and ventricular tachyarrhythmias, intrathoracic impedance and heart failure decompensation in CRT-D Patients," Journal of Cardiac Failure 2007; 13 (6) Suppl.; S131-132.
Wonisch et al., "Continuous haemodynamic monitoring during exercise in patients with pulmonary hypertension," Int J Cardiol. Jun. 8, 2005;101(3):415-420.
Wynne et al., "Impedance cardiography: a potential monitor for hemodialysis," Journal of Surgical Research 2006, 133(1):55-60.
Yancy "Current approaches to monitoring and management of heart failure," Rev Cardiovasc Med 2006; 7 Suppl 1:S25-32.
Ypenburg et al., "Intrathoracic Impedance Monitoring to Predict Decompensated Heart Failure," Am J Cardiol 2007, 99(4):554-557.
Yu et al., "Intrathoracic Impedance Monitoring in Patients With Heart Failure: Correlation With Fluid Status and Feasibility of Early Warning Preceding Hospitalization," Circulation. 2005;112:841-848.
Zannad et al., "Incidence, clinical and etiologic features, and outcomes of advanced chronic heart failure: The EPICAL Study," J Am Coll Cardiol, 1999; 33(3):734-742.
Zile, "Heart failure with preserved ejection fraction: is this diastolic heart failure?" J Am Coll Cardiol, 2003; 41(9):1519-1522.
International Search Report mailed Jun. 4, 2011, PCT/US2011/030991, 6 pages.

(56) References Cited

OTHER PUBLICATIONS

U.S. Appl. No. 13/639,822, filed Oct. 5, 2012, Non-Final Office Action mailed Oct. 8, 2013, 45 pages. Inventors: Katra et al.

U.S. Appl. No. 13/639,822, filed Oct. 5, 2012, Non-Final Office Action mailed May 16, 2014, 24 pages. Inventors: Katra et al.

Williams et al., "How do different indicators of cardiac pump function impact upon the long-term prognosis of patients which chronic heart failure?" American Heart Journal (Nov. 2005) 150 (5): 983e1-983e6.

Written Opinion (PCT/ISA/237) for related International Application No. PCT/US2011/030991 mailed on Jul. 4, 2011.

* cited by examiner

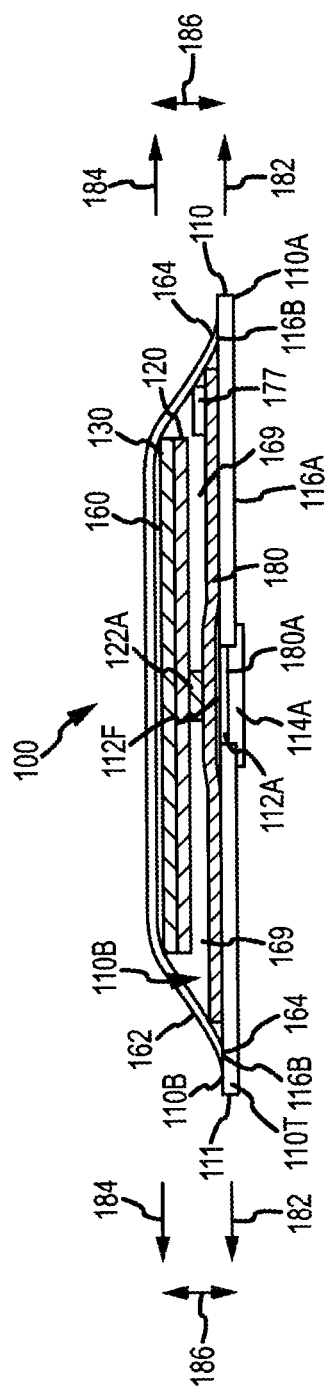
FIG.2A1

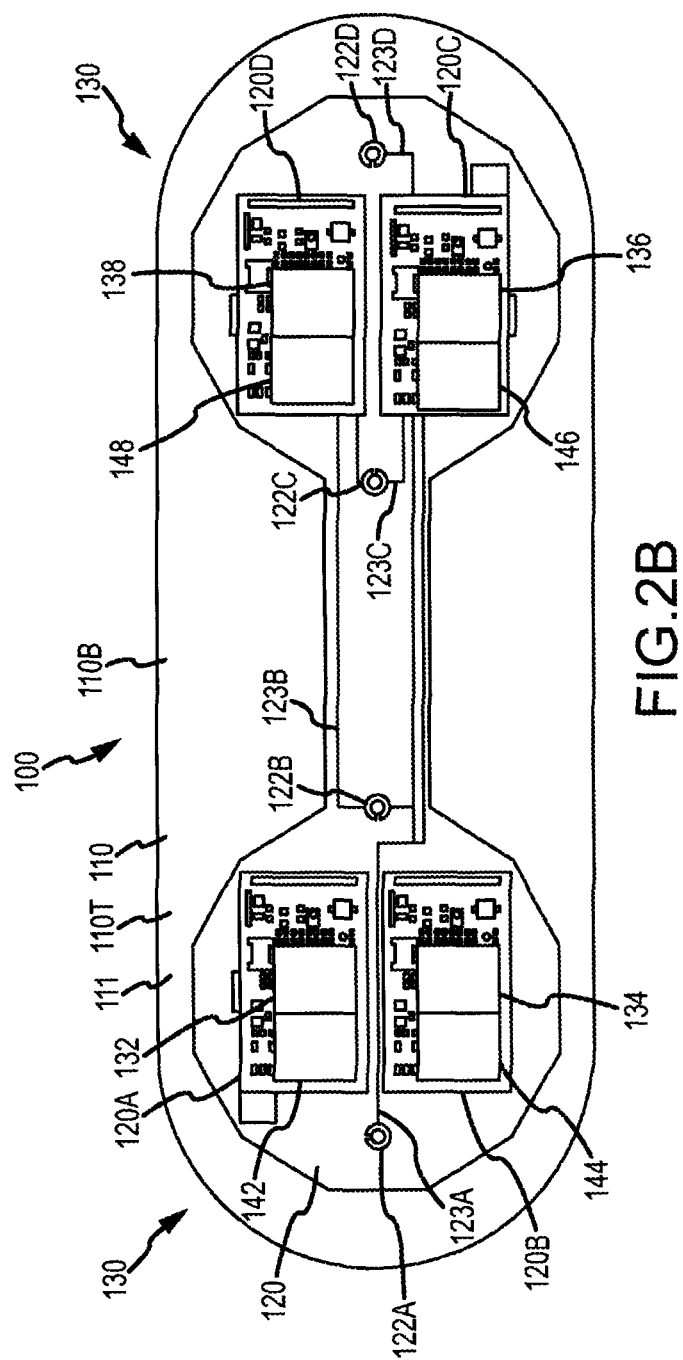
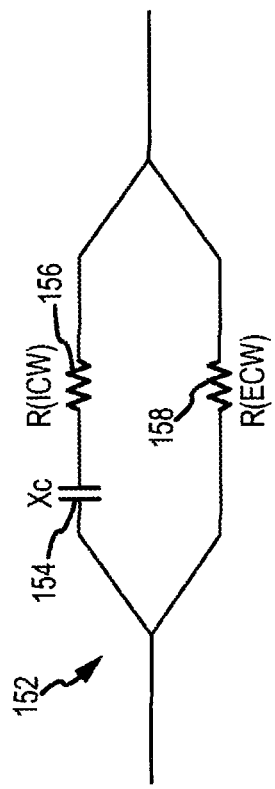
FIG.2B
FIG.2B1

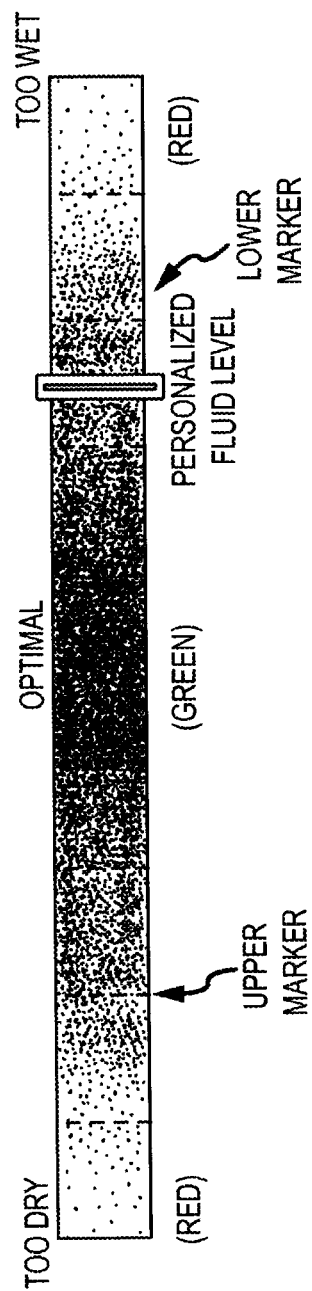

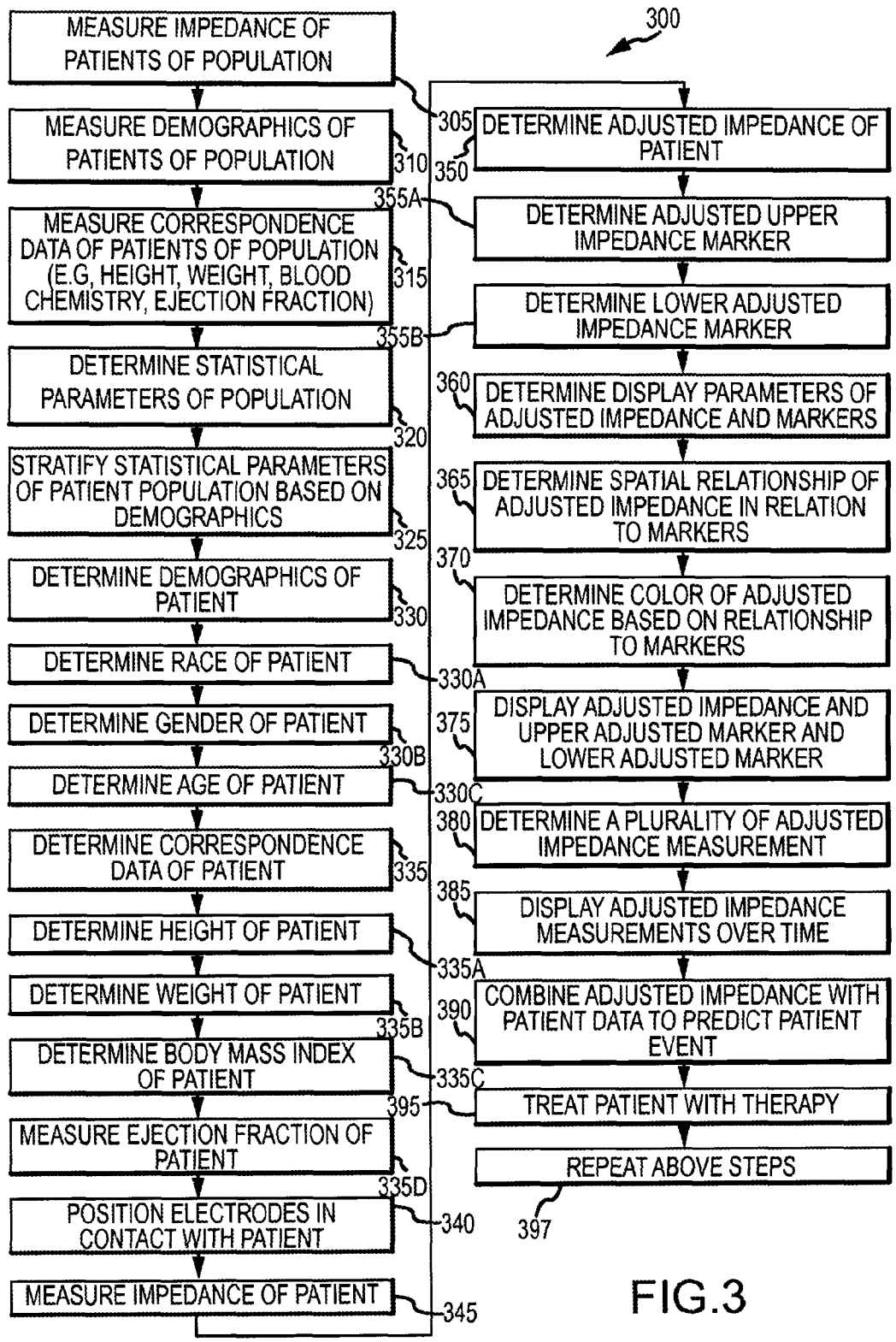

METHOD AND APPARATUS FOR PERSONALIZED PHYSIOLOGIC PARAMETERS

This application claims priority from provisional U.S. patent application Ser. No. 61/321,040, titled "Method and Apparatus for Personalized Physiologic Parameters" and filed Apr. 5, 2010, the entire disclosure of which is hereby incorporated by reference herein for all purposes.

BACKGROUND OF THE INVENTION

The present invention relates to monitoring and treatment of people and animals, and more specifically to patient monitoring and treatment of disease. Although embodiments make specific reference to monitoring impedance and electrocardiogram signals with an adherent patch, the system methods and device described herein may be applicable to many applications in which physiological monitoring is used, for example wireless physiological monitoring with implantable devices for extended periods.

Patients are often treated for diseases and/or conditions associated with a compromised status of the patient, for example a compromised physiologic status such as heart disease. In some instances a patient may have suffered a heart attack and require care and/or monitoring after release from the hospital. While such long term care may be at least partially effective, many patients are not sufficiently monitored and eventually succumb to cardiac decompensation, or heart failure. One example of a device that may be used to monitor a patient is the Holter monitor, or ambulatory electrocardiography device. Although such a device may be effective in measuring electrocardiography, such measurements alone may not be sufficient to reliably detect and/or avoid an impending cardiac decompensation.

In addition to measuring heart signals with electrocardiograms, known physiologic measurements include impedance measurements. For example, transthoracic impedance measurements can be used to measure hydration and respiration. Although transthoracic measurements can be useful, such measurements may use electrodes that are positioned across the midline of the patient, and may be somewhat uncomfortable and/or cumbersome for the patient to wear. Also, known methods of using hydration as a measure of impedance can be subject to error in at least some instances.

Work in relation to embodiments of the present invention suggests that known methods and apparatus for long term monitoring of patients may be less than ideal to detect and/or avoid an impending cardiac decompensation. In at least some instances, cardiac decompensation can be difficult to detect, for example in the early stages. Although bioimpedance and other physiological parameters have been used to assess HF condition and track patient improvement or worsening, at least some of the current methods and apparatus may not predict an impending patient event and can result in false positives in at least some instances.

Therefore, a need exists for improved patient monitoring. Ideally, such improved patient monitoring would avoid at least some of the short-comings of the present methods and devices.

BRIEF SUMMARY OF THE INVENTION

Embodiments of the present invention provide improved methods and apparatus for patient monitoring and treatment. In many embodiments, patient measurement data is combined with demographic or physiological data of the patient to determine an output that can be used to diagnose and treat the patient. For example a customized output can be determined based the demographics of the patient, physiological data of the patient, and data of a population of patients. The patient population data may correspond to data that can influence the data measured from the patient such that the output determined with the patient data and the patient population data is less sensitive to patient characteristics and can be used more effectively by a treating physician. For example, the measured patient data may correspond to hydration of the patient, such as impedance of the patient, and the output may comprise a hydration indicator based patient the impedance of the patient and data that can influence the impedance measurement such as patient demographic data and patient data corresponding to fat. The patient demographic data may comprise one or more gender, age or race, and the patient data corresponding to fat may comprise one or more measurements related to fat of the patient such as the height and weight, the body mass index (BMI), or the percent fat based on imaging. The output determined based on the patient data and the population data may comprise one or more of a hydration indicator, an adjusted impedance, the hydration indicator over time, or an event prediction.

In a first aspect, embodiments of the present invention provide an apparatus to monitor a patient. The apparatus comprises at least two electrodes coupled to circuitry to measure an impedance of the patient. At least one processor receives the measured impedance and patient data, and the at least one processor is configured to determine an output based on the impedance and the patient data.

In many embodiments, the patient data corresponds to a demographic of the patient. The patient demographic may correspond to one or more of a gender of the patient, an age of the patient, or a race of the patient.

In many embodiments, the patient data corresponds to fat of the patient. The patient data corresponding to fat of the patient comprising one or more of a percent body fat of the patient, a body mass index, a height of the patient, a weight of the patient, a caliper measure of the fat of the patient, a tape measure test of the patient, a near infrared interactance, images of the patient to determine fat, dual energy x-ray absorptiometry (DXA), expansion based on body volume, body average density measurement, a second impedance measurement of the patient, an anthropometeric measurement of body fat, a circumference of the patient, a circumference of a body part, a thickness of a skin fold, or an estimate of body density.

In many embodiments, the output comprises customized patient data based on patient data corresponding to fat of the patient and at least one patient demographic comprising one or more of a sex, a race, or an age of the patient.

In many embodiments, the patient data corresponds to an ejection fraction of the patient.

In many embodiments, the patient data comprises one or more of blood pressure, creatinine, blood urea nitrogen (BUN), troponin, ck-mb (creatinine kinase-MB), or a previous event of the patient.

In many embodiments, the output comprises one or more of a patient hydration indicator, an adjusted impedance, a patient population statistic adjusted based on the patent data, the hydration indicator over time, or a patient event prediction output.

In many embodiments, the output may comprise the patient hydration indicator. The at least one processor can be configured to increase an hydration amount of the patient hydration indicator based on the impedance measurement and in response to a decrease of fat of the patient, and the at least one processor can be configured to decrease the hydration amount of the patient hydration indicator based on the impedance measurement and in response to an increase of the fat of the patient.

The hydration indicator may comprise an adjusted impedance of the patient, and the adjusted impedance may correspond inversely to the hydration of the patient.

In many embodiments, the output comprises the adjusted impedance. The at least one processor can be configured to determine the adjusted impedance so as to correspond to an increase of at least about one half ohm per unit increase of body mass index and so as to correspond to a decrease of at least about one half ohm per unit decrease of body mass index. The at least one processor can be configured to determine the adjusted impedance so as to correspond to an increase of at least about one ohm per unit increase of body mass index and so as to correspond to a decrease of at least about one ohm per unit decrease of body mass index.

In many embodiments, the output comprises a spot check output based on a spot check impedance measurement of the patient and the patient data.

In many embodiments, the output comprises an acute output based on an acute impedance measurement of the patient and the patient data.

In many embodiments, the output comprises the patient population statistic adjusted based on the patient data. The output may comprise a first marker and a second marker, in which the first marker is determined based on data of a population of patients and the patient data and the second marker is determined based on the data of the population of patients and the patient data. The first marker may correspond to dehydration of the patient, and the second marker corresponding to excess body fluid of the patient. The first marker may comprise an upper adjusted impedance marker corresponding to dehydration of the patient based on the data of the population of patients, and the second marker may comprise a lower adjusted impedance marker corresponding to excessive hydration of the patient based on the data of the population of patients.

In many embodiments, the at least one processor is configured to determine a first hydration marker based on the patient data and a second hydration marker based on the patient data, the first hydration marker indicating dehydration of the patient, the second hydration marker indicating excess hydration. The at least one processor can be coupled to a display to show the hydration indicator in relation to the first hydration marker and the second hydration marker. The at least one processor can be coupled to a color display and configured to show on the display the hydration indicator in spatial and color relation to the first hydration marker and the second hydration marker. The at least one processor can be configured to show green along a first region of the display extending between the first marker and the second marker configured to show red along a second region of the display disposed away from the first region.

In many embodiments, the output comprises the hydration indicator over time and wherein the hydration indicator over time comprises a plurality of hydration indicators based on a plurality of impedance measurements at least one day apart.

In many embodiments, the output comprises the patient event prediction output. The patient event prediction output may comprise a signal corresponding to prediction of an impending cardiac event of the patient based on the hydration indicator and the patient data. The event prediction signal may comprise a signal to predict an impending cardiac decompensation of the patient based on the adjusted impedance and the patient data.

In many embodiments, the circuitry is coupled to the at least two electrodes to measure the impedance with at least one frequency within a range from about 1 kHz to about 50 kHz. The at least one frequency comprises a bandwidth of no more than about 5 kHz.

In many embodiments, the apparatus further comprises one or more of a cardioverter, an implantable cardioverter-defibrillator (ICD), cardiac a defibrillator, a resynchronization therapy defibrillator (CRT-D) or a pacemaker coupled to the at least one processor to treat the patient.

In many embodiments, the at least two electrodes comprise implantable electrodes. One of the at least two electrodes comprises a housing of the apparatus.

In many embodiments, the at least two electrodes comprise gel electrodes to adhere to a skin of the patient.

In another aspect, embodiments of the present invention provide a method of monitoring a patient. An impedance of the patient is measured, and a patient output is determined based on the measured impedance and a patient data.

In another aspect, embodiments of the present invention provide an apparatus to monitor a patient having a body fluid. The apparatus comprises means for determining an output based on patient data.

BRIEF DESCRIPTION OF THE DRAWINGS

FIGS. 2A and 2A1 show an exploded view and a side cross-sectional view, respectively, of embodiments of the adherent device with a temperature sensor affixed to the gel cover;

FIG. 2B shows a printed circuit board and electronic components over the adherent patch, as in FIG. 2A;

FIG. 2B1 shows an equivalent circuit that can be used to determine optimal frequencies for determining patient hydration, according to embodiments of the present invention;

FIG. 2D shows a viewable display showing an adjusted impedance corresponding to a personalized fluid level disposed between an upper adjusted marker and a lower adjusted marker;

FIG. 3 shows a method of monitoring a patient according to embodiments of the present invention;

DETAILED DESCRIPTION OF THE INVENTION

Embodiments as described herein provide apparatus and methods for adjusting physiological parameters measured by a patient measurement device so as to determine a personalized value for the assessment of the patient, for example of a heart failure (HF) condition.

The methods and apparatus may comprised instructions of a computer program embodied on a computer readable medium so as to operate in accordance with algorithm that uses specific and unique parameters from a patient in order to implement a patient specific and personalized output for HF assessment and care. In many embodiments, the output may comprise a range of normal and abnormal physiological parameters that are adjusted so as to comprise specific and unique evaluation of the condition of the patient.

For example, a patient's demographics and characteristics (e.g. race, gender, weight, BMI, etc.) can be used in a formula derived from population data, to yield a patient specific outcomes target. These target values can be used as initial conditions for treatment or as an ideal endpoint for care. The embodiments as described herein may also include the display of patient data relative to population data; and such display can be made to the patient, caregiver, physician, or other health care professional.

In many embodiments, unique demographic and characteristic information from a patient can be input into an assessment system (input peripheral of the adherent device system). The information input to the system can modify measured values in accordance with an algorithm, select an appropriate algorithm parameter range or select a separate algorithm subroutine that would be most appropriate for that specific patient with a specific disease condition, or combinations thereof. This information is useful for incorporation into a disease tracking or prediction algorithm implemented in accordance with instructions of a computer program. The input information can be used to set the initial conditions of an event prediction algorithm, and can influence the characteristics and/or thresholds of the algorithm.

In many embodiments, the input information can be displayed to the physician relative to values that are appropriate for that patient. This display allows the physician to have an assessment of a patient status relative to a range of values that are appropriate and specific for that patient. Deviation from such values can signify and quantify a change in patient status such as either an improvement or worsening in disease condition in a manner that is specific to that patient. This patient specific information is useful for long term monitoring of patient condition, medication compliance and disease stability.

As used herein the term data encompasses information.

Figure 1:
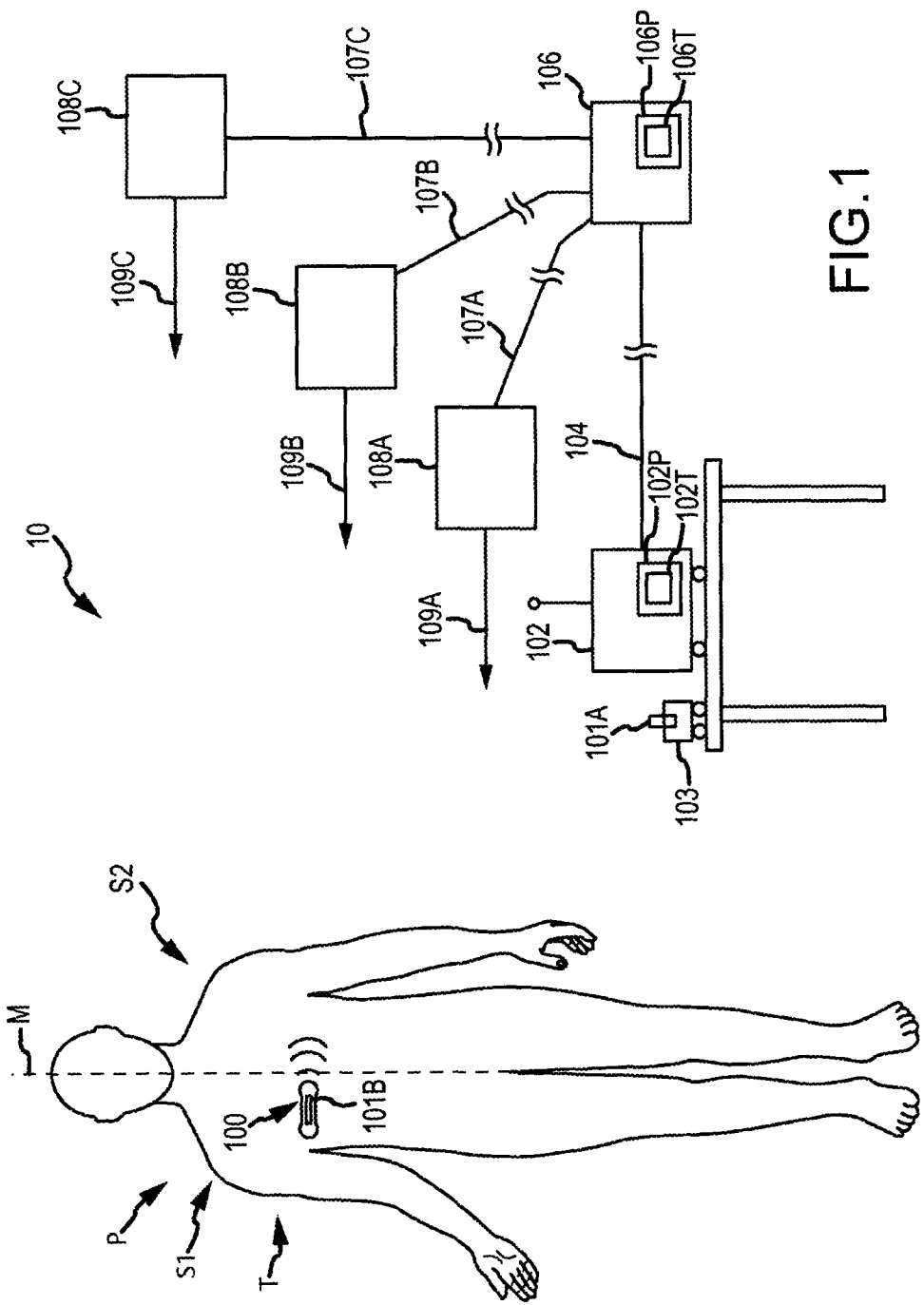
FIG. 1 shows a patient and a monitoring system comprising a patient measurement device, according to embodiments of the present invention.

FIG. 1 shows a patient P and a monitoring system 10. Patient P comprises a midline M, a first side S1, for example a right side, and a second side S2, for example a left side. Monitoring system 10 comprises a patient measurement device to monitor the patient which may comprise an implantable device 100I or an adherent device 100, for example. Adherent device 100 can be adhered to a patient P at many locations, for example thorax T of patient P. In many embodiments, the adherent device may adhere to one side of the patient, from which side data can be collected. Work in relation with embodiments of the present invention suggests that location on a side of the patient can provide comfort for the patient while the device is adhered to the patient. The monitoring system 10 and adherent device 100 may comprise components as described in U.S. Pub. No. US-2009-0076345-A1, entitled "Adherent Device with Multiple Physiological Sensors", and U.S. Pub. No. US-2009-0076344-A1, entitled "Multi-sensor Patient Monitor to Detect Impending Cardiac Decompensation", the full disclosures of which are incorporated herein by reference and suitable for combination in accordance with some embodiments of the present invention as described herein.

Adherent device 100 can wirelessly communicate with remote center 106. The communication may occur directly (via a cellular or Wi-Fi network), or indirectly through intermediate device or gateway 102. The gateway 102 may comprise components of the zLink™, a small portable device similar to a cell phone that wirelessly transmits information received from PiiX™ to Corventis, commercially available from Corventis Inc. of San Jose, Calif. The gateway 102 may consist of multiple devices, which can communicate wired or wirelessly with remote center 106 in many ways, for example with a connection 104 which may comprise an Internet connection and/or with a cellular connection. Remote center 106 may comprise Corventis Web Services, a hosted application for data analysis and storage that also includes the Corventis website (www.corventis.com), which enables secure access to physiological trends and clinical event information for interpretation and diagnosis. In many embodiments, monitoring system 10 comprises a distributed processor system with at least one processor comprising a tangible medium of device 100, at least one processor 102P of gateway 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Remote center 106 can be in communication with a health care provider communication device 108A with a communication system 107A, such as the Internet, an intranet, phone lines, wireless and/or satellite phone. Health care provider communication device 108A, for example for a family member, can be in communication with patient P with a communication, as indicated by arrow 109A. Remote center 106 can be in communication with a health care professional, for example with a physician 108B communication device, with a communication system 107B, such as the Internet, an intranet, phone lines, wireless and/or satellite phone. Physician communication device 108B can be in communication with patient P with communication, for example with a two way communication system, as indicated by arrow 109B. The PDA may comprise a tangible medium having instruction of a computer program embodied thereon to display the patient data to the physician. Remote center 106 can be in communication with an emergency responder device 108C, for example a communication device for a 911 operator and/or paramedic, with a communication system 107C. In many embodiments, instructions are transmitted from remote site 106 to a processor supported with the adherent patch on the patient, and the processor supported with the patient can receive updated instructions for the patient treatment and/or monitoring, for example while worn by the patient. Emergency responder device 108C can travel with the responder to the patient as indicated by arrow 109C. Thus, in many embodiments, monitoring system 10 comprises a closed loop system in which patient care can be monitored and implemented from the remote center in response to signals from the adherent device.

Each of the above described communication devices may comprise a display coupled to a processor having a tangible medium comprising a memory with instructions of a computer program embodied thereon, for example a personal digital assistant (PDA) such as a smart phone, for example a iPhone™, or Blackberry™.

In many embodiments, adherent device 100 may continuously monitor physiological parameters, communicate wirelessly with a remote center, and provide alerts when necessary. The adherent patch may attach to the patient's thorax and contains sensing electrodes, battery, memory, logic, and wireless communication capabilities. In some embodiments, remote center 106 receives the patient data and applies a patient evaluation algorithm, for example the prediction algorithm to predict patient physiological or mental deterioration. In some embodiments, the algorithm may comprise an algorithm to predict impending patient physiological or mental deterioration, for example based on decreased hydration and activity. When a flag is raised, the center may communicate with the patient, hospital, nurse, and/or physician to allow for therapeutic intervention, for example to prevent further physiological or mental deterioration.

Adherent device 100 may be affixed and/or adhered to the body in many ways. For example, with at least one of the following an adhesive tape, a constant-force spring, suspenders around shoulders, a screw-in microneedle electrode, a pre-shaped electronics module to shape fabric to a thorax, a pinch onto roll of skin, or transcutaneous anchoring. Patch and/or device replacement may occur with a keyed patch (e.g. two-part patch), an outline or anatomical mark, a low-adhesive guide (place guide|remove old patch|place new patch|remove guide), or a keyed attachment for chatter reduction. The patch and/or device may comprise an adhesiveless embodiment (e.g. chest strap), and/or a low-irritation adhesive for sensitive skin. The adherent patch and/or device can comprise many shapes, for example at least one of a dogbone, an hourglass, an oblong, a circular or an oval shape.

In many embodiments, adherent device 100 may comprise a reusable electronics module with replaceable disposable patches, and each of the replaceable patches may include a battery. The adherent device 100 may comprise components of the PiiX™, an unobtrusive, water-resistant, patient-worn device that adheres to the skin and automatically collects and transmits physiological information, commercially available from Corventis Inc. of San Jose, Calif. In some embodiments, the device may have a rechargeable module, and may use dual battery and/or electronics modules, wherein one module 101A can be recharged using a charging station 103 while the other module 101B is placed on the adherent patch with connectors. In some embodiments, the gateway 102 may comprise the charging module, data transfer, storage and/or transmission, such that one of the electronics modules can be placed in the gateway 102 for charging and/or data transfer while the other electronics module is worn by the patient.

System 10 can perform the following functions: initiation, programming, measuring, storing, analyzing, communicating, predicting, and displaying. The adherent device may contain a subset of the following physiological sensors: bioimpedance, respiration, respiration rate variability, heart rate (ave, min, max), heart rhythm, heart rate variability (HRV), heart rate turbulence (HRT), heart sounds (e.g. S3), respiratory sounds, blood pressure, activity, posture, wake/sleep, orthopnea, temperature/heat flux, and weight. The activity sensor may comprise one or more of the following: ball switch, accelerometer, minute ventilation, HR, bioimpedance noise, skin temperature/heat flux, BP, muscle noise, posture.

Figure 1B:
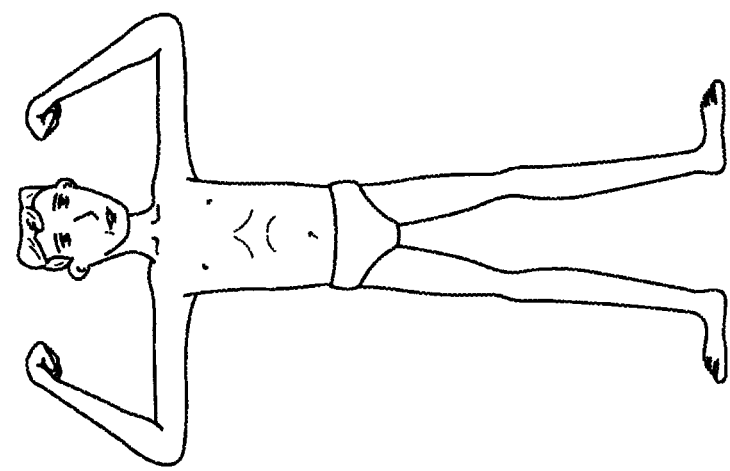
FIG. 1B shows a second patient suitable for monitoring in accordance with embodiments.
Figure 1A:
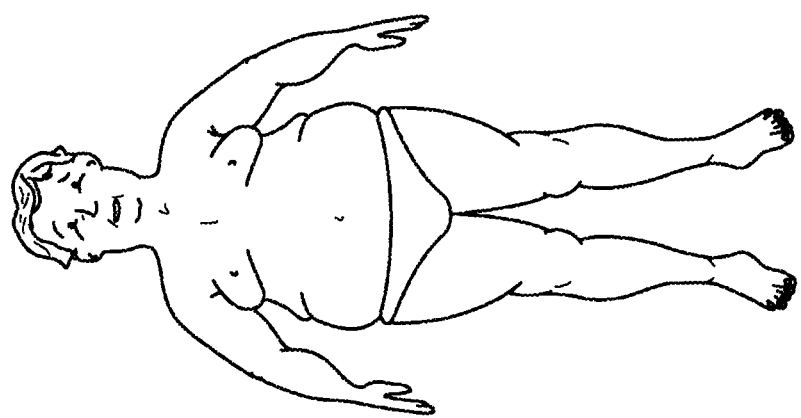
FIG. 1A shows a first patient suitable for monitoring in accordance with embodiments.
Figure 1C:
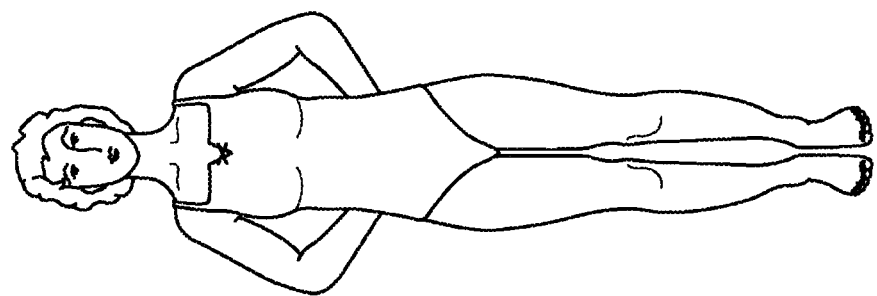
FIG. 1C shows a third patient suitable for monitoring in accordance with embodiments.
Figure 1D:
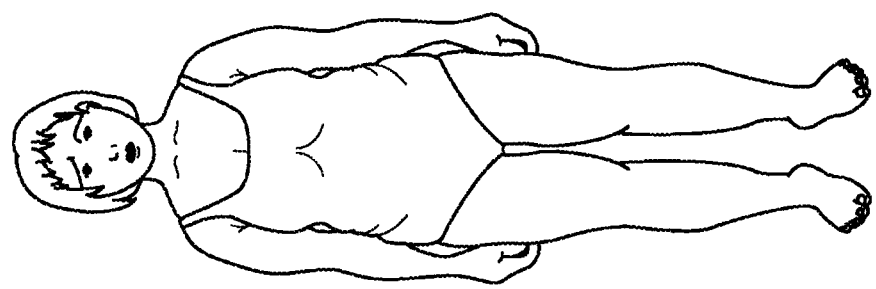
FIG. 1D shows a fourth patient suitable for monitoring in accordance with embodiments.

FIG. 1A shows a first patient suitable for monitoring.
FIG. 1B shows a second patient suitable for monitoring.
FIG. 1C shows a third patient suitable for monitoring.
FIG. 1D shows a fourth patient suitable for monitoring.

Each of the patients shown in FIGS. 1A to 1D may have different physical attributes, such that it can be helpful to determine the output based on the data of the patient. For example, the patients shown in FIGS. 1A and 1B comprise men and the patients shown in FIGS. 1C and 1D comprise women. Each of the patients may have a body mass index determined based on the height and weight of the patient.

Work in relation to embodiments indicates patient characteristics can influence the measurements of the patient. For example, patient demographics such as age, gender and race can be related to the measurements of the patient.

Physiology of the patient can also influence the measurements. For example fat comprising adipose tissue, fat molecules, fat cells and combinations thereof can influence impedance measurements. The fat may comprise a layer of tissue disposed under the skin that can influence the impedance measured through the skin of the patient. For example, electrical current passed through the fat tissue can increase the measured impedance of the patient. Alternatively or in combination, the fat can be disposed in the internal tissues of the patient. For example, fat molecules can permeate internal tissues and may influence impedance measurements of implanted electrodes passing an electrical current through the internal tissues or of electrodes disposed on the skin passing current through the internal tissue. For example, fat may increase the measured impedance of a patient having normal hydration such that the measured impedance is abnormally high, for example, when the patient has normal hydration and would appear dehydrated based on an impedance measurement alone.

Figure 2A:
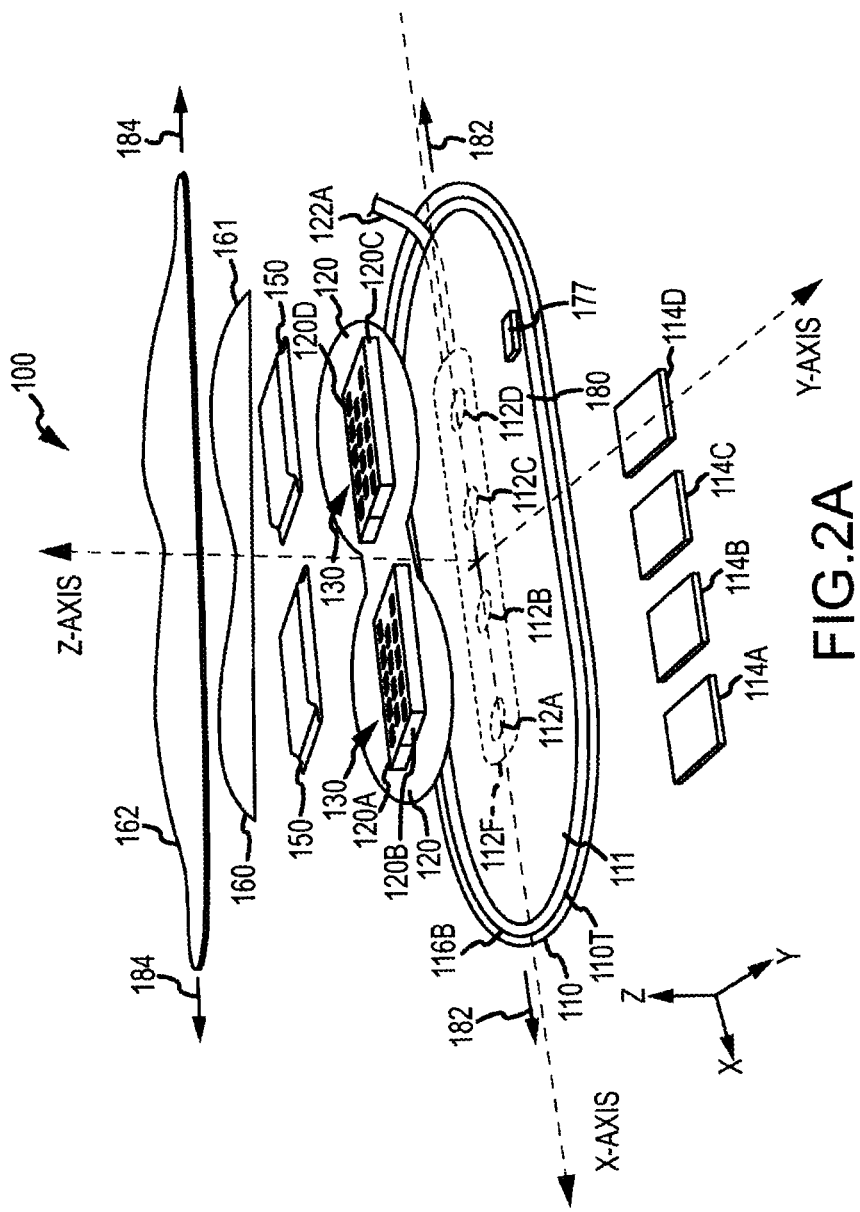

FIGS. 2A and 2A1 show a side cross-sectional view and an exploded view, respectively, of embodiments of the adherent device. The adherent device 100 may comprise an adherent patch 110 with an adhesive 116B, electrodes 112A, 112B, 112C, 112D with gels 114A, 114B, 114C, 114D, gel cover 180, temperature sensor 177, cover 162, and a printed circuit board (PCB) 120 with various circuitry for monitoring physiological sensors, communicating wirelessly with a remote center, and providing alerts when necessary. The adherent device 100 comprises at least two electrodes comprising two or more of electrodes 112A, 112B, 112C and 112D. Adherent device 100 may comprise a maximum dimension, for example a maximum length from about 4 to 10 inches, a maximum thickness along a profile of the device from about 0.2 inches to about 0.6 inches, and a maximum width from about 2 to about 4 inches.

The adherent patch 110 comprises a first side, or a lower side 110A, that is oriented toward the skin of the patient when placed on the patient. The adherent patch 110 may also comprise a tape 110T which is a material, preferably breathable, with an adhesive 116A to adhere to patient P. Electrodes 112A, 112B, 112C and 112D are affixed to adherent patch 110. In many embodiments, at least four electrodes are attached to the patch. Gels 114A, 114B, 114C and 114D can each be positioned over electrodes 112A, 112B, 112C and 112D, respectively, to provide electrical conductivity between the electrodes and the skin of the patient. Adherent patch 100 also comprises a second side, or upper side 110B. In many embodiments, electrodes 112A, 112B, 112C and 112D extend from lower side 110A through adherent patch 110 to upper side 110B. An adhesive 116B can be applied to upper side 110B to adhere structures, for example a breathable cover, to the patch such that the patch can support the electronics and other structures when the patch is adhered to the patient.

In many embodiments, adherent patch 110 may comprise a layer of breathable tape 110T, for example a tricot-knit polyester fabric, to allow moisture vapor and air to circulate to and from the skin of the patient through the tape. In many embodiments, breathable tape 110T comprises a backing material, or backing 111, with an adhesive. In many embodiments, the backing is conformable and/or flexible, such that the device and/or patch does not become detached with body movement. In many embodiments, the adhesive patch may comprise from 1 to 2 pieces, for example 1 piece. In many embodiments, adherent patch 110 comprises pharmacological agents, such as at least one of beta blockers, ace inhibiters, diuretics, steroid for inflammation, antibiotic, antifungal agent, and cortisone steroid. Patch 110 may comprise many geometric shapes, for example at least one of oblong, oval, butterfly, dogbone, dumbbell, round, square with rounded corners, rectangular with rounded corners, or a polygon with rounded corners. In specific embodiments, a thickness of adherent patch 110 is within a range from about 0.001" to about 0.020", length of the patch is within a range from about 2" to about 10", and width of the patch is within a range from about 1" to about 5".

In many embodiments, the adherent device 100 comprises a temperature sensor 177 disposed over a peripheral portion of gel cover 180 to allow the temperature near the skin to be measured through the breathable tape and the gel cover. Temperature sensor 177 can be affixed to gel cover 180 such that the temperature sensor can move when the gel cover stretches and tape stretch with the skin of the patient. Temperature sensor 177 may be coupled to temperature sensor circuitry 144 through a flex connection comprising at least one of wires, shielded wires, non-shielded wires, a flex circuit, or a flex PCB. The temperature sensor can be affixed to the breathable tape, for example through a cutout in the gel cover with the temperature sensor positioned away from the gel pads. A heat flux sensor can be positioned near the temperature sensor for example to measure heat flux through to the gel cover.

The adherent device comprises electrodes 112A, 112B, 112C and 112D configured to couple to tissue through apertures in the breathable tape 110T. Electrodes 112A, 112B, 112C and 112D can be fabricated in many ways, for example printed on a flexible connector 112F, such as silver ink on polyurethane. In some embodiments, the electrodes may comprise at least one of carbon-filled ABS plastic, Ag/AgCl, silver, nickel, or electrically conductive acrylic tape. The electrodes may comprise many geometric shapes to contact the skin, for example at least one of square, circular, oblong, star shaped, polygon shaped, or round. In specific embodiments, a dimension across a width of each electrodes is within a range from about 002" to about 0.050". In specific embodiments, the two inside electrodes may comprise force, or current electrodes, with a center to center spacing within a range from about 20 to about 50 mm. In specific embodiments, the two outside electrodes may comprise measurement electrodes, for example voltage electrodes, and a center-center spacing between adjacent voltage and current electrodes is within a range from about 15 mm to about 35 mm. Therefore, in many embodiments, a spacing between inner electrodes may be greater than a spacing between an inner electrode and an outer electrode.

In many embodiments, gel 114A, or gel layer, comprises a hydrogel that is positioned on electrode 112A and provides a conductive interface between skin and electrode, so as to reduce impedance between electrode/skin interface. The gel may comprise water, glycerol, and electrolytes, pharmacological agents, such as beta blockers, ace inhibiters, diuretics, steroid for inflammation, antibiotic, and antifungal agents. Gels 114A, 114B, 114C and 114D can be positioned over electrodes 112A, 112B, 112C and 112D, respectively, so as to couple electrodes to the skin of the patient. The flexible connector 112F comprising the electrodes can extend from under the gel cover to the PCB to connect to the PCB and/or components supported thereon. For example, flexible connector 112F may comprise flexible connector 122A to provide strain relief.

A gel cover 180, or gel cover layer, for example a polyurethane non-woven tape, can be positioned over patch 110 comprising the breathable tape to inhibit flow of gels 114A-114D through breathable tape 110T. Gel cover 180 may comprise at least one of a polyurethane, polyethylene, polyolefin, rayon, PVC, silicone, non-woven material, foam, or a film. Gel cover 180 may comprise an adhesive, for example an acrylate pressure sensitive adhesive, to adhere the gel cover to adherent patch 110. In many embodiments, the gel cover can regulate moisture of the gel near the electrodes so as to keeps excessive moisture, for example from a patient shower, from penetrating gels near the electrodes. A PCB layer, for example the flex PCB 120, or flex PCB layer, can be positioned over gel cover 180 with electronic components 130 connected and/or mounted to the flex PCB 120, for example mounted on flex PCB so as to comprise an electronics layer disposed on the flex PCB layer. In many embodiments, the gel cover may avoid release of excessive moisture form the gel, for example toward the electronics and/or PCB modules. In many embodiments, a thickness of gel cover is within a range from about 0.0005" to about 0.020". In many embodiments, gel cover 180 can extend outward from about 0-20 mm from an edge of gels. Gel layer 180 and breathable tape 110T comprise apertures 180A, 180B, 180C and 180D through which electrodes 112A-112D are exposed to gels 114A-114D.

In many embodiments, device 100 includes a printed circuitry, for example a PCB module that includes at least one PCB with electronics component mounted thereon. The printed circuit may comprise polyester film with silver traces printed thereon. Rigid PCB's 120A, 120B, 120C and 120D with electronic components may be mounted on the flex PCB 120. In many embodiments, the PCB module comprises two rigid PCB modules with associated components mounted therein, and the two rigid PCB modules are connected by flex circuit, for example a flex PCB. In specific embodiments, the PCB module comprises a known rigid FR4 type PCB and a flex PCB comprising known polyimide type PCB. Batteries 150 may be positioned over the flex PCB and electronic components. Batteries 150 may comprise rechargeable batteries that can be removed and/or recharged. A cover 162 may be placed over the batteries, electronic components and flex PCB. In specific embodiments, the PCB module comprises a rigid PCB with flex interconnects to allow the device to flex with patient movement. The geometry of flex PCB module may comprise many shapes, for example at least one of oblong, oval, butterfly, dogbone, dumbbell, round, square, rectangular with rounded corners, or polygon with rounded corners. In specific embodiments the geometric shape of the flex PCB module comprises at least one of dogbone or dumbbell. The PCB module may comprise a PCB layer with flex PCB 120 that can be positioned over gel cover 180 and electronic components 130 connected and/or mounted to flex PCB 120. In many embodiments, the adherent device may comprise a segmented inner component, for example the PCB, for limited flexibility.

In many embodiments, an electronics housing 160 encapsulates the electronics layer. Electronics housing 160 may comprise an encapsulant, such as a dip coating, which may comprise a waterproof material, for example silicone, epoxy, other adhesives and/or sealants. In many embodiments, the PCB encapsulant protects the PCB and/or electronic components from moisture and/or mechanical forces. The encapsulant may comprise silicone, epoxy, other adhesives and/or sealants. In some embodiments, the electronics housing may comprising metal and/or plastic housing and potted with aforementioned sealants and/or adhesives.

In many embodiments, cover 162 can encase the flex PCB, electronics, and/or adherent patch 110 so as to protect at least the electronics components and the PCB. In some embodiments, cover 162 can be adhered to adherent patch 110 with an adhesive 164 or adhesive 116B on an underside of cover 162. In many embodiments, cover 162 attaches to adherent patch 110 with adhesive 116B, and cover 162 is adhered to the PCB module with an adhesive 161 on the upper surface of the electronics housing. Cover 162 can comprise many known biocompatible cover materials, for example silicone, an outer polymer cover to provide smooth contour without limiting flexibility, a breathable fabric, or a breathable water resistant cover. In some embodiments, the breathable fabric may comprise polyester, nylon, polyamide, and/or elastane (Spandex™). Work in relation to embodiments of the present invention suggests that these coatings can be important to keep excessive moisture from the gels near the electrodes and to remove moisture from body so as to provide patient comfort.

In many embodiments, cover 162 can be attached to adherent patch 110 with adhesive 116B such that cover 162 stretches and/or retracts when adherent patch 110 stretches and/or retracts with the skin of the patient. For example, cover 162 and adherent patch 110 can stretch in two dimensions along the length and width of the adherent patch with the skin of the patient, and stretching along the length can increase spacing between electrodes. Stretching of the cover and adherent patch 110 can extend the time the patch is adhered to the skin as the patch can move with the skin. Electronics housing 160 can be smooth and allow breathable cover 162 to slide over electronics housing 160, such that motion and/or stretching of cover 162 is slidably coupled with housing 160. The PCB can be slidably coupled with adherent patch 110 that comprises breathable tape 110T, such that the breathable tape can stretch with the skin of the patient when the breathable tape is adhered to the skin of the patient, for example along two dimensions comprising the length and the width.

The breathable cover 162 and adherent patch 110 comprise breathable tape that can be configured to couple continuously for at least one week the at least one electrode to the skin so as to measure breathing of the patient. The breathable tape may comprise the stretchable breathable material with the adhesive and the breathable cover may comprises a stretchable breathable material connected to the breathable tape, as described above, such that both the adherent patch and cover can stretch with the skin of the patient. Arrows 182 show stretching of adherent patch 110, and the stretching of adherent patch can be at least two dimensional along the surface of the skin of the patient. As noted above, connectors 122A-122D between PCB 130 and electrodes 112A-112D may comprise insulated wires that provide strain relief between the PCB and the electrodes, such that the electrodes can move with the adherent patch as the adherent patch comprising breathable tape stretches. Arrows 184 show stretching of cover 162, and the stretching of the cover can be at least two dimensional along the surface of the skin of the patient.

The PCB 120 may be adhered to the adherent patch 110 comprising breathable tape 110T at a central portion, for example a single central location, such that adherent patch 110 can stretched around this central region. The central portion can be sized such that the adherence of the PCB to the breathable tape does not have a substantial effect of the modulus of the composite modulus for the fabric cover, breathable tape and gel cover, as described above. For example, the central portion adhered to the patch may be less than about 100 mm$^2$, for example with dimensions that comprise no more than about 10% of the area of patch 110, such that patch 110 can stretch with the skin of the patient. Electronics components 130, PCB 120, and electronics housing 160 are coupled together and disposed between the stretchable breathable material of adherent patch 110 and the stretchable breathable material of cover 160 so as to allow the adherent patch 110 and cover 160 to stretch together while electronics components 130, PCB 120, and electronics housing 160 do not stretch substantially, if at all. This decoupling of electronics housing 160, PCB 120 and electronic components 130 can allow the adherent patch 110 comprising breathable tape to move with the skin of the patient, such that the adherent patch can remain adhered to the skin for an extended time of at least one week.

An air gap 169 may extend from adherent patch 110 to the electronics module and/or PCB, so as to provide patient comfort. Air gap 169 allows adherent patch 110 and breathable tape 110T to remain supple and move, for example bend, with the skin of the patient with minimal flexing and/or bending of PCB 120 and electronic components 130, as indicated by arrows 186. PCB 120 and electronics components 130 that are separated from the breathable tape 110T with air gap 169 can allow the skin to release moisture as water vapor through the breathable tape, gel cover, and breathable cover. This release of moisture from the skin through the air gap can minimize, and even avoid, excess moisture, for example when the patient sweats and/or showers. Gap 169 extends from adherent patch 110 to the electronics module and/or PCB a distance within a range from about 0.25 mm to about 4 mm.

In many embodiments, the adherent device comprises a patch component and at least one electronics module. The patch component may comprise adherent patch 110 comprising the breathable tape with adhesive coating 116A, at least one electrode, for example electrode 112A and gel 114A. The at least one electronics module can be separable from the patch component. In many embodiments, the at least one electronics module comprises the flex PCB 120, electronic components 130, electronics housing 160 and cover 162, such that the flex PCB, electronic components, electronics housing and cover are reusable and/or removable for recharging and data transfer, for example as described above. In specific embodiments, the electronic module can be adhered to the patch component with a releasable connection, for example with Velcro™, a known hook and loop connection, and/or snap directly to the electrodes. Monitoring with multiple adherent patches for an extended period is described in U.S. Pub. No. 2009-0076345-A1, published on Mar. 19, 2009, the full disclosure of which has been previously incorporated herein by reference, and which adherent patches and methods are suitable for combination in accordance with embodiments described herein.

The adherent device 100, shown in FIG. 2A, may comprise an X-axis, Y-axis and Z-axis for use in determining the orientation of the adherent device 100 and/or the patient P. Electric components 130 may comprise a 3D accelerometer. As the accelerometer of adherent device 100 can be sensitive to gravity, inclination of the patch relative to an axis of the patient can be measured, for example when the patient stands. Vectors from a 3D accelerometer can be used to determine the orientation of a measurement axis of the patch adhered on the patient and can be used to determine the angle of the patient, for example whether the patient is laying horizontally or standing upright, when measured relative to the X-axis, Y-axis and/or X-axis of adherent device 100.

FIG. 2B shows a PCB and electronic components over adherent patch 110. In some embodiments, PCB 120, for example a flex PCB, may be connected to electrodes 112A, 112B, 112C and 112D of FIG. 2A with connectors 122A, 122B, 122C and 122D, respectively, and may include traces 123A, 123B, 123C and 123D that extend to connectors 122A, 122B, 122C and 122D. In some embodiments, connectors 122A-122D may comprise insulated wires and/or a film with conductive ink that provide strain relief between the PCB and the electrodes. Examples of structures to provide strain relief are also described in U.S. Pub. No. 2009-0076345-A1, entitled "Adherent Device with Multiple Physiological Sensors", filed on Sep. 12, 2008 as noted above.

Electronic components 130 comprise components to take physiologic measurements, transmit data to remote center 106 and receive commands from remote center 106. In many embodiments, electronics components 130 may comprise known low power circuitry, for example complementary metal oxide semiconductor (CMOS) circuitry components. Electronics components 130 comprise a temperature sensor, an activity sensor and activity circuitry 134, impedance circuitry 136 and electrocardiogram circuitry, for example ECG circuitry 138. In some embodiments, electronics circuitry 130 may comprise a microphone and microphone circuitry 142 to detect an audio signal, such as heart or respiratory sound, from within the patient.

Electronics circuitry 130 may comprise a temperature sensor, for example a thermistor in contact with the skin of the patient, and temperature sensor circuitry 144 to measure a temperature of the patient, for example a temperature of the skin of the patient. A temperature sensor may be used to determine the sleep and wake state of the patient, which may decrease during sleep and increase during waking hours. Work in relation to embodiments of the present invention suggests that skin temperature may affect impedance and/or hydration measurements, and that skin temperature measurements may be used to correct impedance and/or hydration measurements. In some embodiments, increase in skin temperature or heat flux can be associated with increased vasodilation near the skin surface, such that measured impedance measurement decreased, even through the hydration of the patient in deeper tissues under the skin remains substantially unchanged. Thus, use of the temperature sensor can allow for correction of the hydration signals to more accurately assess the hydration, for example extra cellular hydration, of deeper tissues of the patient, for example deeper tissues in the thorax.

Activity sensor and activity circuitry 134 can comprise many known activity sensors and circuitry. In many embodiments, the accelerometer comprises at least one of a piezoelectric accelerometer, capacitive accelerometer or electromechanical accelerometer. The accelerometer may comprises a 3-axis accelerometer to measure at least one of an inclination, a position, an orientation or acceleration of the patient in three dimensions. Work in relation to embodiments of the present invention suggests that three dimensional orientation of the patient and associated positions, for example sitting, standing, lying down, can be very useful when combined with data from other sensors, for example hydration data.

Impedance circuitry 136 can generate both hydration data and respiration data. In many embodiments, impedance circuitry 136 is electrically connected to electrodes 112A, 112B, 112C and 112D of FIG. 2A in a four pole configuration, such that electrodes 112A and 112D comprise outer electrodes that are driven with a current and comprise force electrodes that force the current through the tissue. The current delivered between electrodes 112A and 112D generates a measurable voltage between electrodes 112B and 112C, such that electrodes 112B and 112C comprise inner, sense, electrodes that sense and/or measure the voltage in response to the current from the force electrodes. In some embodiments, electrodes 112B and 112C may comprise force electrodes and electrodes 112A and 112D may comprise sense electrodes. The voltage measured by the sense electrodes can be used to measure the impedance of the patient and determine the respiration rate and/or hydration of the patient. The electrocardiogram circuitry may be coupled to the sense electrodes to measure the electrocardiogram signal, for example as described in U.S. Pub. No. 2009-0076345-A1, entitled "Adherent Device with Multiple Physiological Sensors", published on Mar. 29, 2009, previously incorporated by reference and suitable for combination in accordance with embodiments described herein. In many embodiments, impedance circuitry 136 can be configured to determine respiration of the patient. In specific embodiments, the impedance circuitry can measure the hydration at 25 Hz intervals, for example at 25 Hz intervals using impedance measurements with a frequency from about 0.5 kHz to about 20 kHz.

ECG circuitry 138 can generate electrocardiogram signals and data from two or more of electrodes 112A, 112B, 112C and 112D in many ways. In some embodiments, ECG circuitry 138 is connected to inner electrodes 112B and 122C, which may comprise sense electrodes of the impedance circuitry as described above. In many embodiments, the ECG circuitry may measure the ECG signal from electrodes 112A and 112D when current is not passed through electrodes 112A and 112D.

Electronics circuitry 130 may comprise a processor 146 that can be configured to control a collection and transmission of data from the impedance circuitry electrocardiogram circuitry and the accelerometer. Processor 146 comprises a tangible medium, for example read only memory (ROM), electrically erasable programmable read only memory (EEPROM) and/or random access memory (RAM). Electronic circuitry 130 may comprise real time clock and frequency generator circuitry 148. In some embodiments, processor 146 may comprise the frequency generator and real time clock. In many embodiments, device 100 comprises a distributed processor system, for example with multiple processors on device 100.

In many embodiments, electronics components 130 comprise wireless communications circuitry 132 to communicate with remote center 106. PCB 120 may comprise an antenna to facilitate wireless communication. The antenna may be integral with PCB 120 or may be separately coupled thereto. The wireless communication circuitry can be coupled to the impedance circuitry, the electrocardiogram circuitry and the accelerometer to transmit to a remote center with a communication protocol at least one of the hydration signal, the electrocardiogram signal or the inclination signal. In specific embodiments, wireless communication circuitry 132 is configured to transmit the hydration signal, the electrocardiogram signal and the inclination signal to the remote center either directly or through gateway 102. The communication protocol comprises at least one of Bluetooth, ZigBee, WiFi, WiMAX, IR, amplitude modulation or frequency modulation. In many embodiments, the communications protocol comprises a two way protocol such that the remote center is capable of issuing commands to control data collection.

In many embodiments, the electrodes are connected to the PCB with a flex connection, for example trace 123A, 123B, 123C and 123D of flex PCB 120, so as to provide strain relief between the electrodes 112A, 112B, 112C and 112D and the PCB. In such embodiments, motion of the electrodes relative to the electronics modules, for example rigid PCB's 120A, 120B, 120C and 120D with the electronic components mounted thereon, does not compromise integrity of the electrode/hydrogel/skin contact. In many embodiments, the flex connection comprises at least one of wires, shielded wires, non-shielded wires, a flex circuit, or a flex PCB. In specific embodiments, the flex connection may comprise insulated, non-shielded wires with loops to allow independent motion of the PCB module relative to the electrodes.

FIG. 2B1 shows an equivalent circuit 152 that can be used to determine optimal frequencies for measuring patient hydration. Work in relation to embodiments of the present invention indicates that the frequency of the current and/or voltage at the force electrodes can be selected so as to provide impedance signals related to the extracellular and/or intracellular hydration of the patient tissue. Equivalent circuit 152 comprises an intracellular resistance 156, or R(ICW) in series with a capacitor 154, and an extracellular resistance 158, or R(ECW). Extracellular resistance 158 is in parallel with intracellular resistance 156 and capacitor 154 related to capacitance of cell membranes. In many embodiments, impedances can be measured and provide useful information over a wide range of frequencies, for example from about 0.5 kHz to about 200 KHz. Work in relation to embodiments of the present invention suggests that extracellular resistance 158 can be significantly related extracellular fluid and to patient physiological or mental physiological or mental deterioration, and that extracellular resistance 158 and extracellular fluid can be effectively measured with frequencies in a range from about 0.5 kHz to about 50 kHz, for example from about 0.5 kHz to 20 kHz, for example from about 1 kHz to about 10 kHz. In some embodiments, a single frequency can be used to determine the extracellular resistance and/or fluid. As sample frequencies increase from about 10 kHz to about 20 kHz, capacitance related to cell membranes decrease the impedance, such that the intracellular fluid contributes to the impedance and/or hydration measurements. Thus, many embodiments of the present invention measure hydration with frequencies from about 0.5 kHz to about 50 kHz to determine patient hydration.

As noted herein, fat can influence the impedance measurement and an increase in fat can increase the measured impedance and a decrease in fat can decrease the measured impedance, and the presence of fat can be related to the impedance measured with the equivalent circuit shown in FIG. 2B1.

Figure 2C:
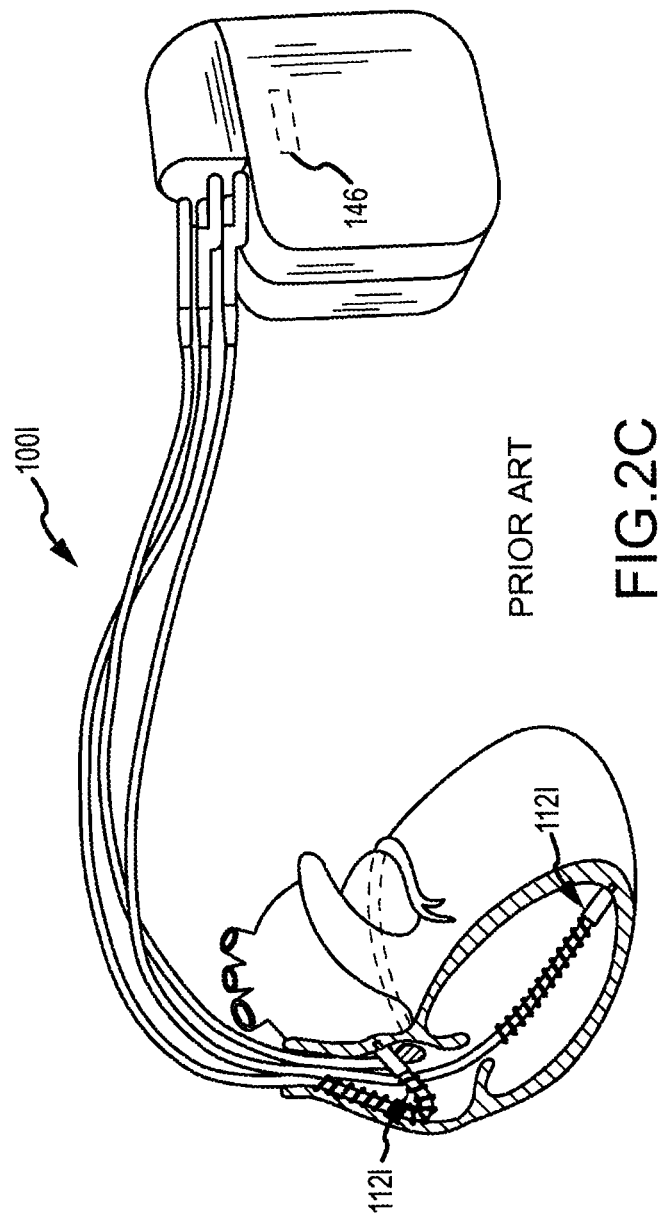
FIG. 2C shows an implantable device suitable for incorporation according to embodiments of the present invention.

FIG. 2C shows a schematic illustration of an implantable device 1001 suitable for incorporation in accordance with embodiments of the present invention. Implantable device 1001 comprises at least two implantable electrodes 1121, and a processor 146. The implantable device 1001 may comprise a component of system 10, and processor 146 may comprise at least one processor of the processor system. The implantable device 1001 may comprise many of the components of the adherent device 100, as described herein.

For example, the implantable device 1001 may comprise components of an implantable medical device as described in U.S. Pat. Pub. No. 20080024293, entitled "ADAPTATIONS TO OPTIVOL ALERT ALGORITHM", in the name of Stylos, published on Jan. 31, 2008. The implantable medical device may include a hermetically sealed enclosure and three leads: a ventricular lead, an atrial/SVC lead, and a coronary sinus/coronary vein lead. The enclosure may contain the electronic circuitry used for generating cardiac pacing pulses for delivering cardioversion and defibrillation shocks and for monitoring the patient's heart rhythm. Examples of such circuitry are known in the art. The ventricular lead may carry three electrodes adjacent its distal end: a ring electrode, an extendable helix electrode mounted retractably within an insulative electrode head, and an elongated coil electrode. The atrial/SVC lead may carry the same three electrodes adjacent its distal end: a ring electrode, an extendible helix electrode mounted retractably within an insulative electrode head, and an elongated coil electrode. The coronary sinus/ coronary vein lead may carry an electrode (illustrated in broken outline) that can be located within the coronary sinus and great vein of the heart. The coronary sinus/coronary vein lead may also carry a ring electrode and a tip electrode adjacent its distal end.

FIG. 2D shows a viewable display showing an hydration indicator disposed between a first upper adjusted marker and a second lower adjusted marker. The first upper marker may correspond to dehydration of the patient can be shown in red a may correspond to a first threshold shown on a first region of the display. The second upper marker may correspond to excessive hydration of the patient can be shown in red a may correspond a first threshold shown on a second portion of the screen. The hydration indicator may comprise a slider disposed between the first marker and the second marker when the patient has normal hydration. The hydration indicator may comprise an adjusted impedance corresponding to a personalized fluid level of the patient. For example, the patient's height and weight can be entered into the at least one processor of the processor system and used to determine a personalized bioimpedance corresponding to a personalized fluid amount or fluid level. The measured bioimpedance can be compared to a heart failure patient population with comparable physical characteristics. The graphical display can show the patient specific fluid status relative to a comparable cohort of patients.

The information can be used in many ways, for example to assess patient status as a point in time measurement, for example upon admission to a hospital or upon discharge from a hospital. The hydration indicator comprising the adjusted bioimpedance can be used to guide patient care such as diuresis and ultrafiltration and to assess response to treatment. The hydration indicator comprising the adjusted bioimpedance can be used to assess remotely the stability of HF disease following discharge and to assess remotely patient compliance and effectiveness with HF medication.

Figure 2E:
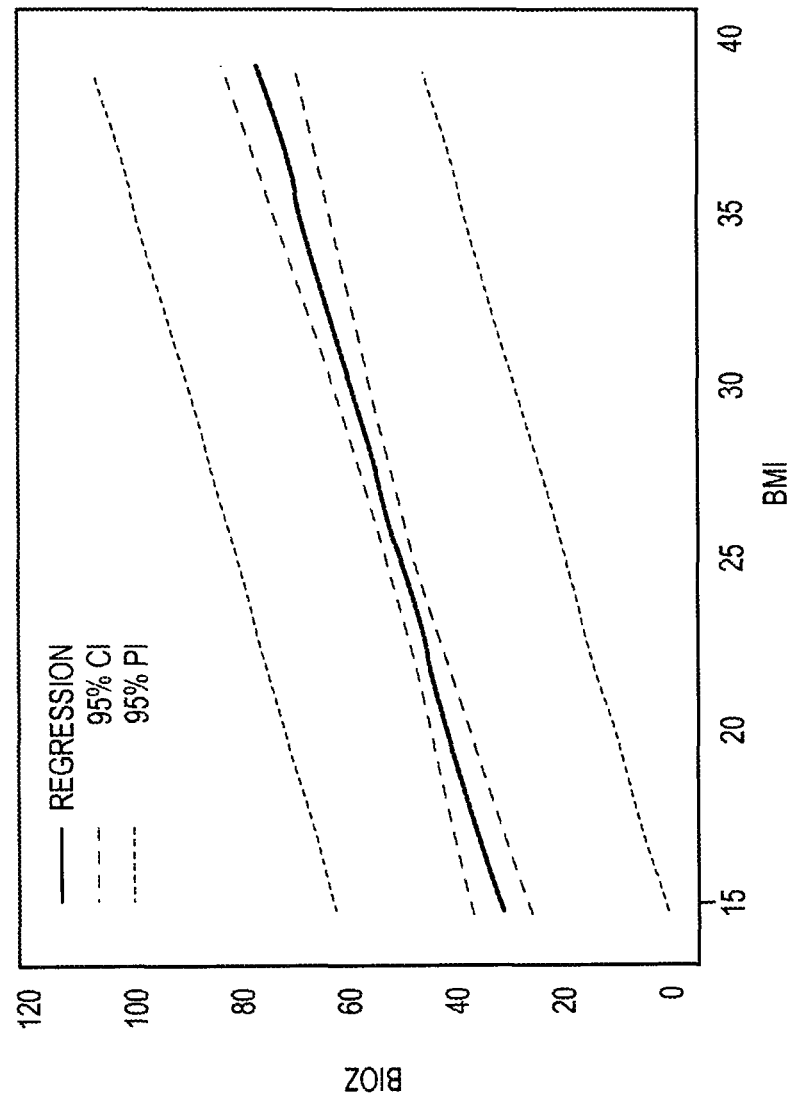
FIG. 2E shows a plot corresponding to statistical parameters of a patient population that can be combined with patient data to generate a display in accordance with embodiments shown in FIG. 2D.

FIG. 2E shows a plot corresponding to statistical parameters of a patient population that can be combined with patient data to generate a display in accordance with embodiments shown in FIG. 2D, for example. The statistical data may correspond to statistics of a patient population such as a regression coefficients that may comprise a slope, offset and fit coefficients that can be used to determine a regression line, confidence intervals and prediction intervals, for example. The display can show the statistical data of the population and the individual patient, so as to help the physician interpret the condition of the patient. For example, the display can show a confidence interval, for example 95% CI, a prediction interval, for example 95% PI and a regression line. The prediction intervals may correspond to the first upper marker and second lower marker shown above, for example, adjusted based on the independent patient parameter such as body mass index.

The data can be stratified based on demographics such as a one or more of race, gender and age, and correspondence among measured patient determined for presentation to the physician. The correspondence of impedance with body mass index can be used to establish the upper and lower markers and "optimal" hydration. For example, the patient body mass index (BMI) and patient population data can be used to determine the prediction interval markers corresponding to the upper and lower markers based on the body mass index, and the regression line can be used to determine the "optimal" hydration based on the body mass index. Similar adjustments can be made to many of the individual patient measurements as described herein based on the patient population data.

Figure 2F:
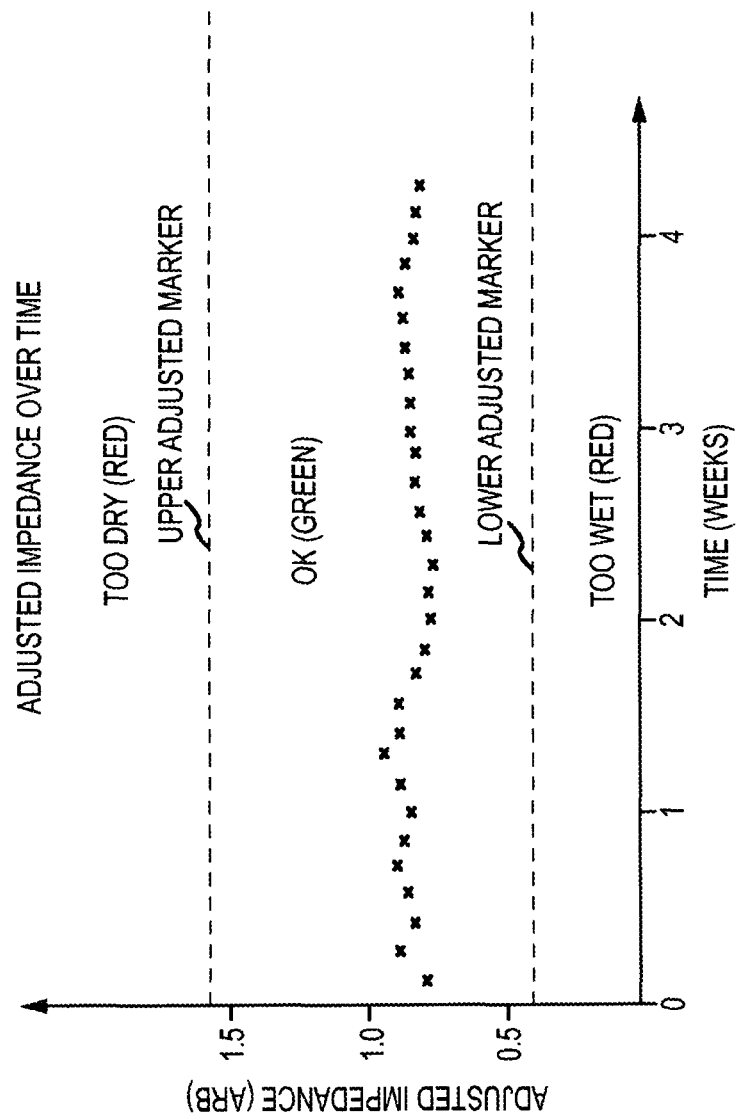
FIG. 2F shows adjusted impedance over time in accordance with embodiments of FIG. 2D and FIG. 2E.

FIG. 2F shows adjusted impedance over time show on a physician device display in accordance with embodiments of FIG. 2D and FIG. 2E. The adjusted impedance over time may comprise a plurality of adjusted impedance measurements, for example daily measurements shown over about four weeks. The adjusted impedance over time may be shown in relation to the upper adjusted marker (too dry) and the lower adjusted marker (too wet). The time course of the patient treatment can be used by the physician to evaluate treatment.

FIG. 3 shows a method 300 of monitoring a patient according to embodiments of the present invention At a step 305, the impedance of a patient population is measured, for example with a patient measurement device for each patient of the population as described herein.

At a step 310, demographics of the individuals of the patient population are measured.

At a step 315, additional data of patients of the population are measured (e.g. height, weight, blood chemistry, ejection fraction) such that correspondence of among the measurement data, demographic data and correspondence data can be determined.

At a step 320, statistical parameters of the patient population are determined.

At a step 325, statistical parameters of the patient population are stratified based on demographics.

At a step 330, the demographics of the individual patient are determined.

At a sub-step, 330A the race of the patient is determined.
At a sub-step 330B, the gender of the patient is determined.
At a sub-step 330C, the age of the patient is determined.
At a step 335 the additional data of the patient is determined (e.g. height, weight, blood chemistry, ejection fraction)

At a sub-step 335A, the height of the patient is determined.
At a sub-step 335B, the weight of the patient is determined.
At a sub-step 335C, the body mass index of the patient is determined.
At a sub-step 335D, the ejection fraction of the patient is determined.
At a step 340, electrodes are positioned in contact with the patient.
At a step 345, the impedance of the patient is measured, for example with electrodes as described above.
At a step 350, an adjusted impedance of the patient is determined, for example a hydration indicator as described above.

At a step 355A, an upper adjusted impedance marker is determined,
At a step 355B, a lower adjusted impedance marker is determined.
At a step 360, display parameters are determined for the adjusted impedance and markers.
At a step 365, spatial relationships are determined for the adjusted impedance in relation to the adjusted impedance markers
At a step 370, a color is determined of the adjusted impedance based on the spatial relationship to the markers, for example.
At a step 375, the adjusted impedance the upper adjusted marker and the lower adjusted marker are shown on the display to the physician.
At a step 380, a plurality of adjusted impedance measurements are determined.
At a step 385, adjusted impedance measurements over time are displayed.
At a step 390, adjusted impedance is combined with patient data to predict an event of the patient, for example a heart failure event of the patient.
At a step 395, the patient is treated with therapy, which may comprise treatment with drugs, electrical stimulation therapy, or combinations thereof.
At a step 397, the above steps can be repeated.

The processor system, as described above, may comprise instructions of a computer program embedded thereon so as to perform many of the steps of the method 300. For example, many of the steps of the method 300 can be performed with the processor system comprising the processor of the patient measurement device, the processor of the gateway and the processor of the remote server. The method 300 can be performed with one or more of the processor of the patient measurement device, the processor of the gateway and the processor of the remote server. Further the steps of the method 300 can be distributed among the processor of the processor system such that each processor performs at least one of the steps or sub-steps of method 300.

It should be appreciated that the specific steps illustrated in FIG. 3 provide a particular method of monitoring a patient in accordance with an embodiment of the present invention. Other sequences of steps may also be performed in accordance with alternative embodiments. For example, alternative embodiments of the present invention may perform the steps outlined above in a different order. Moreover, the individual steps illustrated in FIG. 3 may include multiple sub-steps that may be performed in various sequences as appropriate to the individual step. Alternatively, the multiple sub-steps may be performed as an individual step. Furthermore, additional steps may be added or removed depending on the particular applications. One of ordinary skill in the art would recognize many variations, modifications, and alternatives.

Embodiments as described herein can be incorporated with many commercially available patient monitoring and treatment systems such as the OptiVol™ alert algorithm and computer programs embodying instructions thereof commercially available from Medtronic, the CareLink™ server commercially available from Medtronic, the Latitude™ patient management system commercially available from Boston Scientific, the Merlin™ system commercially available from St. Jude and the MCOT™ commercially available from CardioNet.

Cardiac Event Prediction

According to another aspect, embodiments may find particular application in the prediction of impending cardiac events, for example impending acute decompensated heart failure (ADHF) events. In particular, the accuracy of cardiac event prediction may be significantly enhanced if the prediction is based at least in part on personalized data gathered from a patient, rather than being based merely on norms applicable to large patient populations. In some embodiments, the prediction is based at least in part on data measured over time from the patient, for example impedance data. The prediction may also be based at least in part on descriptive data that indicates at least one descriptive characteristic of the patient, for example any one or any combination of the patient's height, weight, body mass index, or other characteristics.

An adherent device, for example an adherent device such as those described above and shown in FIGS. 2A-2B1, may be adhered to the skin of a patient, and measures a bioimpedance between two or more electrodes of the adherent device. Bioimpedance may also be referred to herein as simply "impedance." The adherent device provides ongoing impedance measurements that can be used to characterize the patient's hydration level, breathing, and other parameters, and to monitor changes in the patient's parameters. One or more of these parameters may be utilized to predict an impending cardiac event. Multi-parameter prediction may have advantages in event prediction accuracy.

As is discussed above, each adherent device may have a finite useful life, and multiple adherent devices may be used serially to monitor a patient over an extended period. For example, each adherent device may remain in place on the patient for about 1 week, after which another adherent device replaces the former one. The data from the multiple adherent devices may be combined into a single, ongoing data set. As is described above, data from the adherent devices may be transmitted to a remote computer where analysis is performed.

The adherent device or devices may make ongoing measurements of a number of different characteristics of the patient, including the patient's bioimpedance, electrocardiogram information, temperature, activity level, posture, hydration, or other characteristics, such as an audio signal characterizing a heart or respiratory sound of the patient.

Some patient data may indicate one or more descriptive characteristics of the patient. This kind of data may also be referred to as "patient descriptive data". For example, patient descriptive data may correspond to the amount of fat in the patient's body, and could include one or more of a percent body fat of the patient, a body mass index, a height of the patient, a weight of the patient, or other information corresponding to the fat of the patient. Patient descriptive data may include demographic information about the patient, for example the patient's sex, race, or age.

In some embodiments, patient descriptive data may be input to the system, for example using a keyboard, key pad, bar code reader, scanner, wired or wireless electronic signal, automated measurement device, or other input mechanism. Patient descriptive data could also be obtained from the patient's medical records, for example by automatic access of medical records stored electronically. Patient descriptive data may be input into the system once at the beginning of a monitoring period, or only occasionally during a monitoring period, as compared with the characteristics measured by the adherent devices on an ongoing basis throughout the monitoring period.

Figure 5:
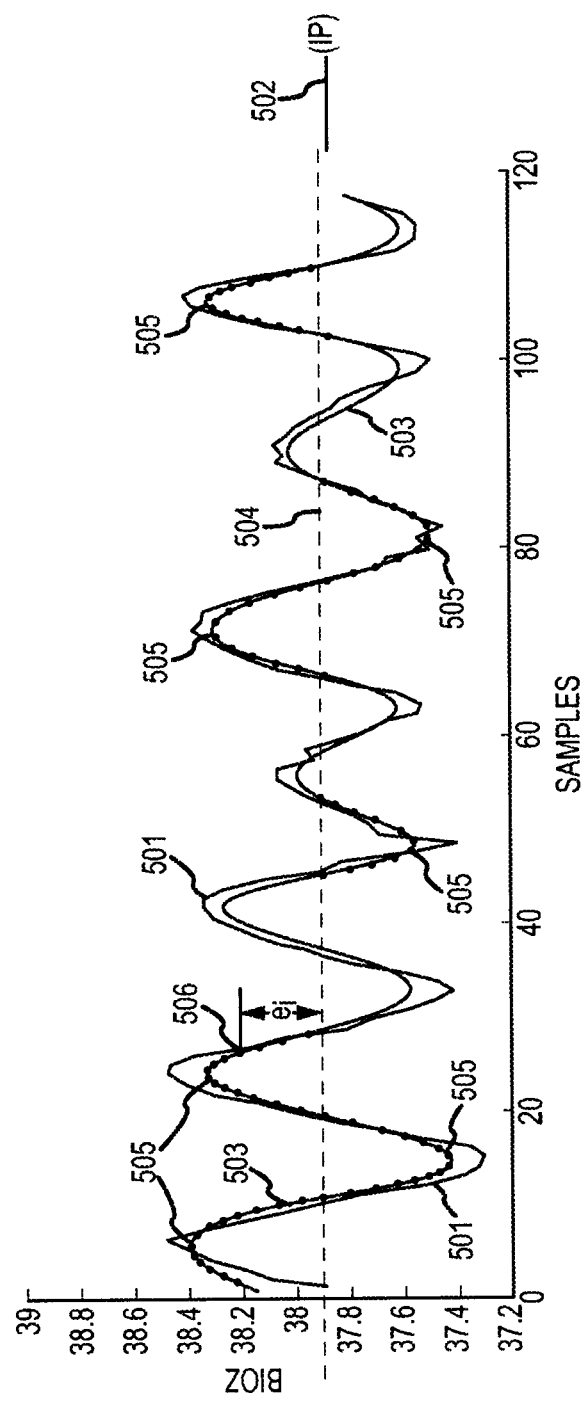
FIG. 5 illustrates reading impedance data (BioZ) from the adherent device in accordance with embodiments.

FIG. 5 illustrates reading impedance data (BioZ) from the adherent device in accordance with embodiments, to determine one reading of an impedance parameter and one reading of a breath parameter. In some embodiments, impedance data from the adherent device are gathered periodically, for example every 5, 10, 15, 20, 30, or 60 minutes, to determine the impedance parameter and the breath parameter. Other intervals between readings may be used. The impedance may be indicative of patient hydration, and the impedance data may also be processed to derive the breath parameter that is indicative of some aspect or combination of aspects of the patient's breathing, for example the patient's breathing rate or the volume of air breathed by the patient in a tidal breath.

In the example of FIG. 5, the impedance is sampled 120 times over the span of 30 seconds, to gather 120 impedance data points. The raw data points from one 30-second sample period are shown in curve 501. Other sampling periods and frequencies could be used. The peaks and valleys in curve 501 correspond to the patient's breathing, and in this particular instance, the patient took about seven breaths while the impedance was being sampled.

To determine one impedance reading from the 120 data points, outliers may be eliminated from the data points, and the median of the remaining points determined. In the example of FIG. 5, the impedance parameter IP 502 derived from this 30-second sampling period is the median of the retained data points. In other embodiments, the impedance data points could be averaged to determine the impedance parameter, or some other process could be used to determine the impedance parameter reading from the data points.

To determine the breath parameter for a particular sampling interval, curve 501 may be first filtered, to smooth the curve in a manner similar to filtered curve 503. In some embodiments, the filtering may be accomplished by convolving a $5^{th}$ order high pass Butterworth filter with a 0.05 Hz cutoff and a $9^{th}$ order low pass Butterworth filter with a 0.4 Hz cutoff and applying the resulting filter function to the data points, although other kinds of filters could be used. The DC component of curve 501 may also be established at axis 504. The local maxima of the absolute value of the filtered points are found, and the peaks having magnitudes in the upper 50% of the peaks are retained—that is, those having the largest magnitudes as measured from axis 504. In the example of FIG. 5, seven peaks 505 are retained. An envelope is defined around each of the peaks, including all of the samples between the respective peak and the neighboring minimum on each side of the peak. A variance of these samples is then computed. In FIG. 5, the samples used for computing the shown with heavy dots. One particular $i^{th}$ sample 506 is labeled, and its magnitude $e_i$ is depicted, as measured from axis 504. The variance is simply the sum of the squares of the magnitudes of the dotted samples. That is, the breath parameter BP derived from this 30-second sampling period is $\Sigma e_i^2$ over all of the dotted data points. The breath parameter BP may be related to the patient's breath volume or breathing effort. The breath parameter values may be further filtered before use. For example, in some embodiments, the breath parameter values are low-pass filtered before use, using an averaging finite impulse response filter of length 20.

Thus, in this embodiment, at the end of each 30-second sampling interval, a single reading of impedance parameter IP and a single reading of breath parameter BP are obtained.

While specific example techniques for computing an impedance parameter and a breath parameter are described above, may other techniques are possible within the scope of the claims. For example, the breath parameter could be computed as an area under curve 501 or curve 503, or the breath parameter could be based on the peak values of curve 501 or curve 503. Techniques for computing an impedance parameter and a breath parameter without generating a curve similar to curve 501 could be utilized. In some embodiments, a breath parameter relating to the patient's breathing rate, breathing effort, or some other aspect of the patient's breathing could be determined.

Figure 6:
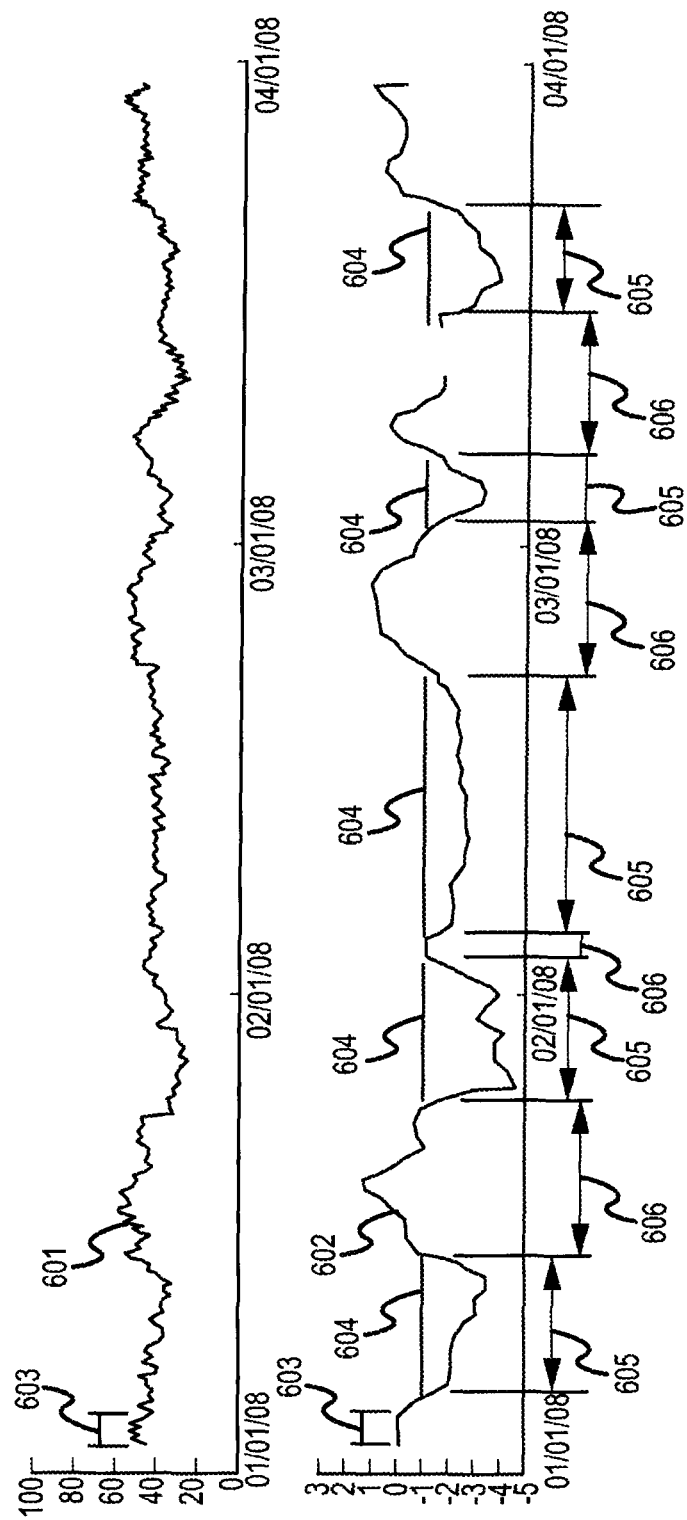
FIG. 6 illustrates an example method of utilizing the impedance parameter readings to derive an impedance flag that may be used in predicting an impending cardiac event.
Figure 7:
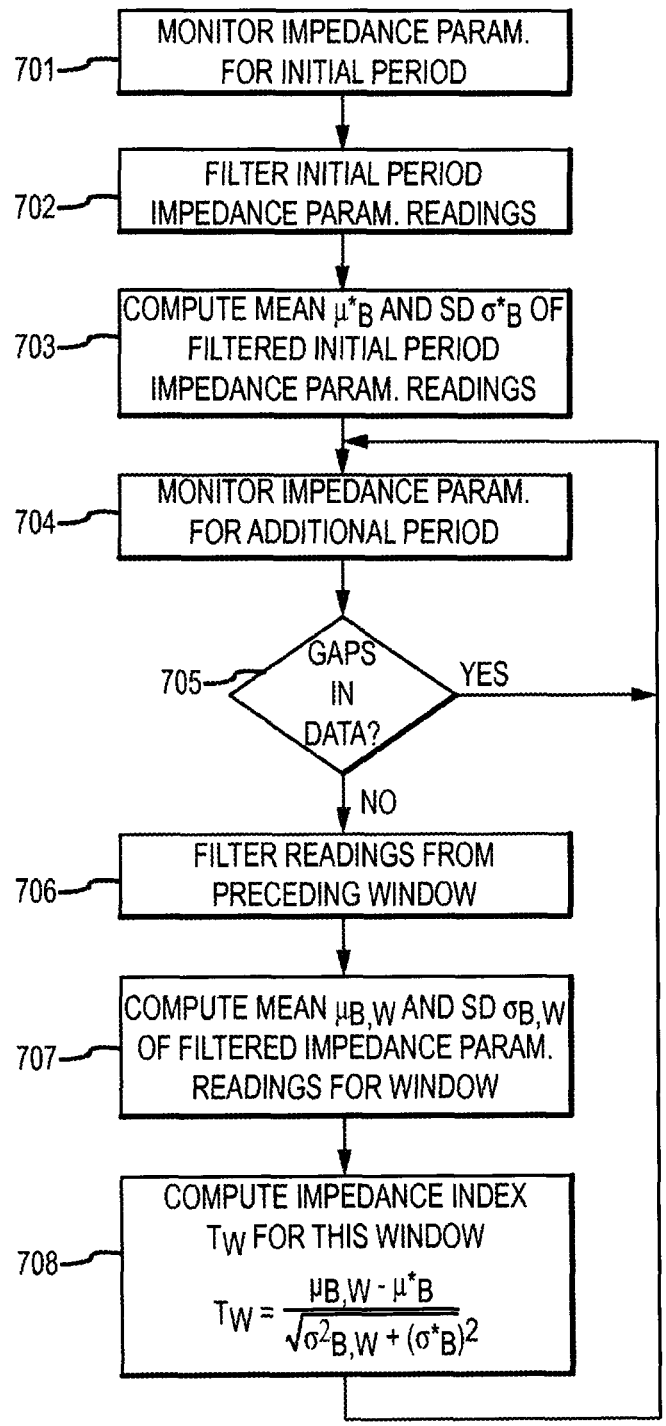
FIG. 7 illustrates a flowchart of one exemplary embodiment for computing a baseline impedance and an impedance index.

FIGS. 6 and 7 illustrate example methods of utilizing the impedance parameter readings to derive a baseline impedance, an impedance index, and an impedance flag that may be used in predicting an impending cardiac event.

In some embodiments, a prediction of an impending cardiac event is based at least in part on relationship of the ongoing measurements of the impedance parameter IP to a patient-specific baseline impedance. Because bioimpedance and patient hydration are related, this parameter may be thought of as a measurement of the amount of fluid in the patient's tissues, and the prediction may be thought of as being based in part on the relationship of the patient's ongoing fluid measurements to a patient-specific baseline fluid measurement.

Turning to FIG. 6, the upper curve 601 schematically represents the impedance parameter readings taken a patient, as described above. Curve 601 is simplified for ease of illustration, and spans about 90 days of monitoring. An actual curve including readings taken over several months may include thousands of readings of impedance.

The impedance parameter readings taken during an initial period at the beginning of monitoring may be used to determine one or more patient-specific baseline values for the patient. For example, in some embodiments, a baseline impedance specific to the patient is computed as the average of the impedance parameter readings taken during the initial period of monitoring. The length of the initial period may be selected as any appropriate time, for example 24 hours, 48 hours, 72 hours, or another suitable time period. The variability of the readings may also be characterized, for example the standard deviation of the impedance parameter readings taken during the initial period may be computed. Some additional filtering may be performed before computing the average and standard deviation.

In some embodiments, patient activity data may be available, indicating whether the patient is resting or active, for example exercising. The activity data may be derived from signals provided by an accelerometer or other activity sensor on the adherent device that also performs the impedance measurements. Preferably, the readings utilized for establishing the baseline impedance (and the baseline breath parameter described below) are taken while the patient is in a state of relatively low activity, and preferably at rest. In other embodiments, the patient's posture may be detected, and utilized in the data gathering. For example, readings utilized for establishing the baseline parameters may preferably be taken while the patient is lying down.

An index may then be computed that is indicative of a change in the impedance parameter relative to the baseline impedance over time. For example, the index may generally track the number of standard deviations (of the initial monitoring period data) by which the current impedance parameter reading departs from the baseline impedance value. The index is then compared with a threshold, and when the index passes the threshold, an impedance flag is generated indicating that the impedance has departed from the baseline value by more than the threshold amount. The flag may be an actual electronic signal, for example a voltage level in a digital electronic circuit, but most often will be a state recognized and recorded by a processor executing program instructions.

The lower curve 602 of FIG. 6 depicts an example impedance index and the results of these computations. As can be seen, during the initial period 603 while the baseline impedance is being established, the deviation from the baseline is taken to be zero. After the initial period 603, the impedance index is tracked and compared with a threshold value. The threshold value may be set at any suitably predictive value, for example −0.6, −0.9, −1.2, −1.5, or another number of standard deviations of the baseline data. The actual threshold value will depend on the particular method used for characterizing the impedance parameter readings during the initial period. For example if a variance of the impedance parameter readings were to be used, then the magnitude of the threshold value may be significantly different than in an embodiment where a standard deviation is used. Any time the index passes or exceeds (goes below) the threshold, the predictive impedance flag 604 indicates that the threshold has been exceeded. This condition can be seen in FIG. 6 during intervals 605. This impedance flag may be utilized alone or in combination with other flags or signals to predict an impending cardiac event. Whenever the impedance index is closer than the threshold value to the baseline impedance, the predictive impedance flag is not raised, for example in intervals 606 shown in FIG. 6.

Further filtering may be performed in the computation of the impedance index. In the exemplary embodiment of FIG. 6, the impedance index is computed periodically from the impedance parameter readings taken during a preceding time window. Any suitable sampling period and window length may be utilized. For example, the impedance index may be computed every ¼ hour, ½ hour, 1 hour, 1.5 hour, 2 hours, or on another suitable schedule, and may be based on impedance parameter readings taken during the previous 12 hours, 24 hours, 36 hours, 48 hours, 60 hours, 72 hours, or another suitable window length. In some embodiments, the variability of the readings obtained during the current window is also considered in the computation of the impedance index. Each window may overlap considerably with the previous one. For example, if the impedance index is computer every ½ hour, and each window is 24 hours long, the each window would overlap by 23.5 hours with the previous window.

FIG. 7 illustrates a flowchart of one exemplary embodiment for computing the baseline impedance and the impedance index 602. In step 701, the impedance parameter is monitored, for example as described above, for the initial period. In step 702, the impedance parameter readings are filtered. In some embodiments, a median filter of having an order between 3 and 15, for example an order of 3, 5, 7, 9, 11, 13, or 15, may be applied to the impedance parameter readings, although other kinds or lengths of filters may be used, or the filtering step may be omitted. In step 703, a mean $\mu^*_B$ and standard deviation $\sigma^*_B$ are computed from the filtered initial period impedance parameter readings. The mean $\mu^*_B$ and standard deviation $\sigma^*_B$ are thus patient-specific baseline values derived from the patient's impedance data. A different patient may have different values. The mean $\mu^*_B$ is an example of a baseline impedance specific to the patient.

In step 704, the impedance parameter is monitored for an additional time period. In step 705, the data from the current window is examined to see if gaps exist. For example, if it is determined that any two adjacent readings were taken more than four hours apart, it may be determined that the data for the current window has gaps, and the data may not be used. In step 706, the readings in the current window are filtered, for example using a $9^{th}$ order median filter or another kind of filter. As before, the filtering step could be omitted. It will be also understood that some of the operations depicted in FIG. 7 may be reordered. For example, the filtering of the readings from the current window could be performed before examining the data to see if gaps exist.

In step 707, the mean $\mu_{B,W}$ and standard deviation $\sigma_{B,W}$ of filtered impedance parameter data from the current window are computed. In step 708, the impedance index $T_W$ is computed as $$T_W = \frac{\mu_{B,W} - \mu_B^*}{\sqrt{\sigma_{B,W}^2 + (\sigma_B^*)^2}}.$$

Generally, impedance index $T_W$ indicates how much the impedance at the current window differs from the patient's patient-specific baseline impedance. A lower value for $T_W$ generally indicates a higher fluid level in the patient's tissues. This example formula accounts for the variance of the readings taken during the current window, as well as the variance of the readings taken during the initial period.

While the example above describes one technique for establishing a baseline impedance parameter and computing an impedance index, many other techniques are possible within the scope of the claims. For example, a baseline impedance parameter may be computed as a median of several readings of an impedance parameter, or even from a single reading. An impedance index may not be based on a number of standard deviations of change from the baseline, but could be based on a simple difference in readings from the baseline, a percentage change from the baseline, or could be computed in any other suitable way.

In some cases, for example in a patient who has had a recent prior cardiac event, the patient's impedance readings may be changing significantly during the initial period during which the baseline values are being established. For this reason, an additional check and optimization may be performed. In one example embodiment, the impedance index values are examined for the first five days of monitoring. If any window during the first five days has an impedance index $T_W$ that departs from the baseline impedance index by a significant amount, and the patient has had a previous cardiac event within the past seven days, then the baseline values for impedance and breath volume may be reset to the values computed for the window having the maximum departure from the baseline impedance index.

Figure 8:
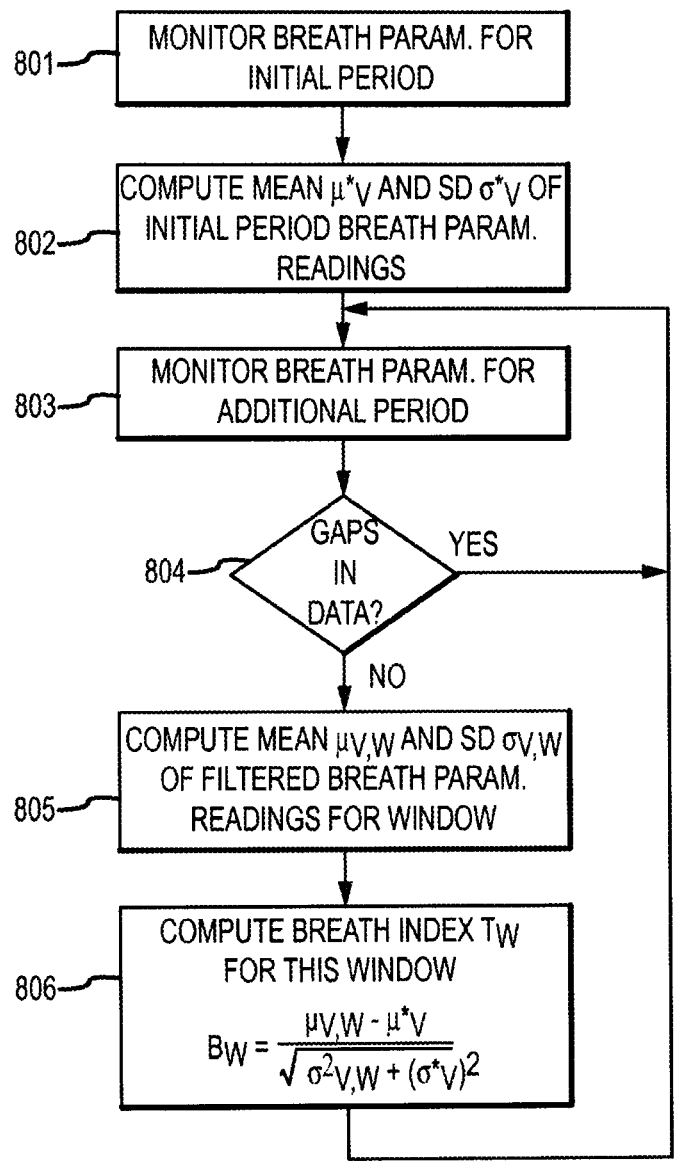
FIG. 8 illustrates a flowchart of one exemplary method of computing a baseline breath parameter and a breath index.

FIG. 8 illustrates a flowchart of one exemplary method of computing a baseline breath parameter and a breath index that may be utilized in predicting a cardiac event. A breath flag is also derived from the breath parameter and the breath index. In some embodiments, the breathing parameter may be monitored in a manner similar to the impedance parameter, and a baseline established and a breath index computed. Prediction of an impending cardiac event may then be based at least in part on relationship of the ongoing measurements of the breath parameter to the patient-specific baseline breath parameter.

In step 801, the breathing parameter is monitored, for example as described above, for the initial period. In step 802, a mean $\mu^*_V$ and standard deviation $\sigma^*_V$ are computed from the initial period breath parameter readings. The mean $\mu^*_V$ and standard deviation $\sigma^*_V$ are patient-specific baseline breath-related values derived from the patient's impedance data. A different patient may have different values.

In step 803, the breath parameter is monitored for an additional time period. In step 804, the data from the previous window is examined to see if gaps exist. For example, if it is determined that any two adjacent readings were taken more than four hours apart, it may be determined that the data for the current window has gaps, and the data may not be used.

In step 805, the mean $\mu_{V,W}$ and standard deviation $\sigma_{V,W}$ of the breath parameter data from the current window are computed. In step 806, the breath index $B_W$ is computed as $$B_W = \frac{\mu_{V,W} - \mu_V^*}{\sqrt{\sigma_{V,W}^2 + (\sigma_V^*)^2}}.$$

Generally, breath index $B_W$ indicates how much the breath parameter at the current window differs from the patient's patient-specific baseline breath parameter. A lower value for $B_W$ generally indicates shallower breathing.

It will be recognized that additional filtering steps may be utilized in the computation of breath index $B_W$.

The relationship of the breath index $B_W$ and the baseline breath parameter value may be tracked to generate a predictive breath flag. For example, a threshold deviation from the baseline may be established, and the breath flag raised when the breath index exceeds the threshold. The threshold may be set at any suitable predictive value, for example, −0.2, −0.3, −0.4, −0.5, or some other level. The actual magnitude of the threshold is dependent on the particular technique used to compute the breath parameter. For example, if a variance of the baseline readings is used rather than a standard deviation, or if a different breath parameter is used, the threshold may be considerably different.

While the example above describes one technique for establishing a baseline breath parameter and computing a breath index, many other techniques are possible within the scope of the claims. For example, a baseline breath parameter may be computed as a median of several readings of a breath parameter, or even from a single reading. A breath index may not be based on a number of standard deviations of change from the baseline, but could be based on a simple difference in readings from the baseline, a percentage change from the baseline, or could be computed in any other suitable way. In other embodiments, the breath parameter may be related to the patient's breathing rate, rather than volume, and the breath index may indicate a change in the patient's breathing rate as compared with a baseline breathing rate.

Figure 9:
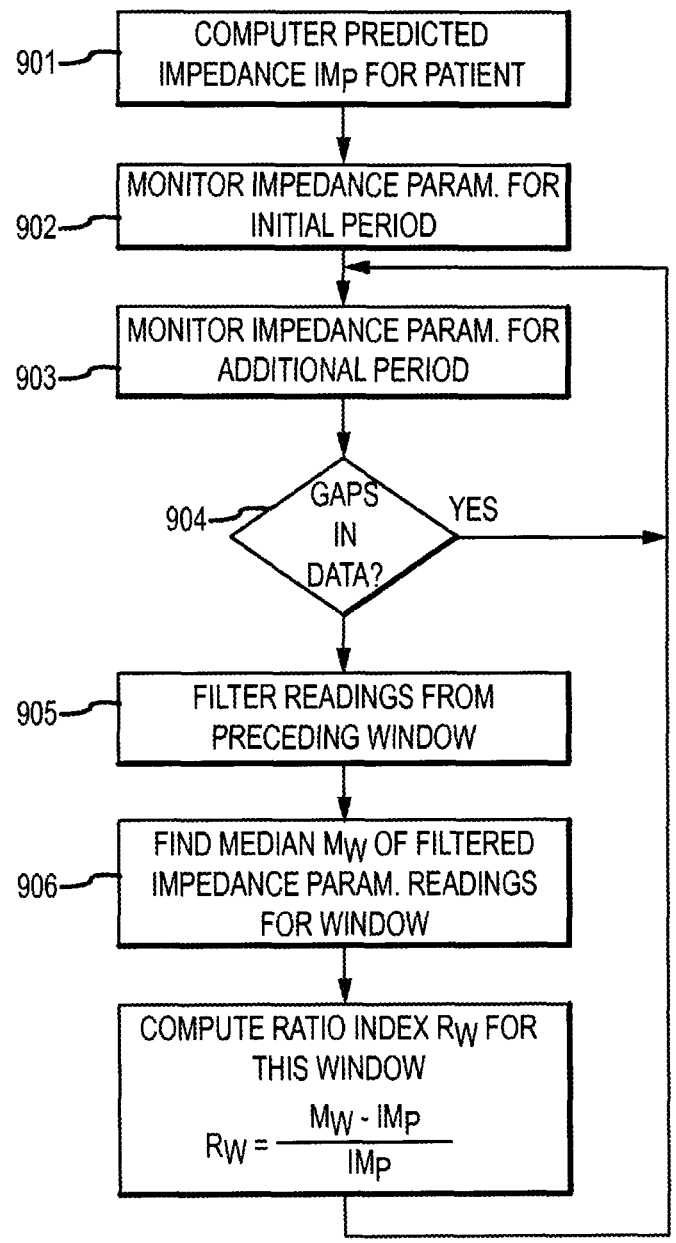
FIG. 9 illustrates a flowchart for computing a ratio index from ongoing measurements of the patient's impedance and the patient's predicted impedance.

FIG. 9 illustrates a method of computing another index that may be utilized in predicting a cardiac event according to embodiments. In the method of FIG. 9, a patient-specific predicted impedance value is computed, and the ongoing measurements of the impedance parameter compared with this predicted value to generate another index that may be utilized in the prediction of an impending cardiac event. In one example embodiment, the predicted impedance is computed from the patient's body mass index (BMI), which is in turn computed from the patient's height and weight.

Figure 4:
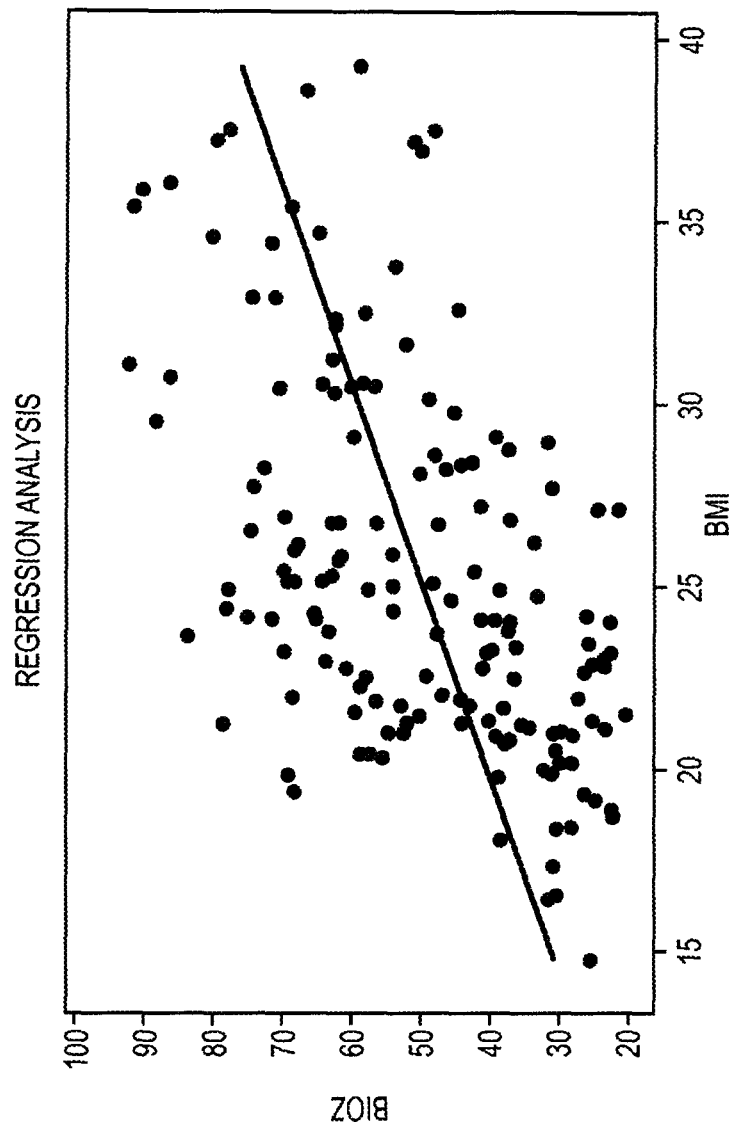
FIG. 4 shows a scatter plot of impedance and body mass index measured with a population of approximately 200 patients, in accordance with embodiments.

Based on the data shown in FIG. 4, a best-fit linear model indicates that in general, the higher a patient's BMI, the higher the patient's predicted impedance. The linear model includes a slope m and an intercept value b, and predicts BioZ from BMI according to the relation Predicted Impedance=$b+m$*BMI.

Depending on the particular population of subjects used to generate the linear model and the fitting technique used, the slope may be between 1.5 and 2.0, and the intercept may be between 3 and 4. For example, the slope m may be approximately 1.5, 1.6, 1.7, 1.8, 1.9, or 2.0, and the intercept value b may be approximately 3.0, 3.2, 3.4, 3.6, 3.8, or 4.0.

FIG. 9 illustrates a flowchart for computing a ratio index from the ongoing measurements of the patient's impedance and the patient's predicted impedance. In step 901, the patient's predicted impedance $IM_P$ is computed, for example as described above. In step 902, the patient's impedance is measured for an initial period. In step 903, the patient's impedance is monitored for an additional time period. In step 904, the impedance data for the current window is examined to see if there are data gaps. If the impedance parameter data is sufficient, it is filtered in step 905. It will be recognized that if the ratio index and the impedance index described above are both to be calculated, that some steps such as filtering steps 706 and 905 are redundant, and need be performed only once. In step 906, the median $M_W$ of the impedance parameter readings in the current window is determined. In step 907, the ratio index $R_W$ is computed as $$R_W = \frac{M_W - IM_P}{IM_P}.$$

Generally, ratio index $R_W$ indicates how much the patient's current impedance parameter differs from the impedance that would be expected for a patient having similar characteristics, such as body mass index.

The ratio index $R_W$ may be tracked to generate a predictive ratio flag. For example, a threshold ratio may be established, and the ratio flag raised when the ratio index exceeds the threshold. The threshold may be set at any suitably predictive level, for example −0.1, −0.2, −0.3, or another value. The actual magnitude of the ratio will depend on the particular method used for computing the predicted impedance and the ratio index.

While the example above describes one technique for establishing a predicted impedance computing a ratio index, many other techniques are possible within the scope of the claims. For example, a predicted impedance may be based on some characteristic of the patient other than BMI, for example a body fat percentage, the patient's weight alone, or some other characteristic or combination of characteristics. A ratio index may be computed using some other technique, rather than a simple difference between the current impedance and the predicted impedance.

In embodiments, any one, any combination, or all of the impedance flag, the breath flag, and the ratio flag may be used to predict events such as impending acute decompensate heart failure.

In some embodiments, a flag is used for prediction only if it has been raised for at least a specified duration threshold. For example, the duration threshold for the impedance flag may be set, and the impedance flag may be considered as present for prediction only if it has been raised continuously for at least the duration threshold. Similar duration thresholds may be set for the breath flag and the ratio flag. The duration thresholds may be set at any suitably predictive values, for example, 1 day, 2 days, 3 days, 4 days, or some other value. The duration thresholds need not all be the same.

The flags may be used or combined in various ways. For example, the impedance flag could be used alone to predict acute decompensated heart failure, with a prediction output generated if the impedance flag has been raised for more than its duration threshold.

However, the accuracy of prediction may be enhanced if multiple variables are considered in the prediction algorithm. In other example embodiments, any two of the impedance flag, the breath flag, and the ratio flag may be combined to generate the prediction output.

In a preferred embodiment, all three of the impedance flag, the breath flag, and the ratio flag are utilized in determining the prediction output, and the flags may be combined as follows:

1) if the impedance flag and the ratio flag are present concurrently, and the breath flag is present for at least some of the time that the impedance flag and the ratio flag are concurrently present, the prediction output is generated to predict impending acute decompensated heart failure;
2) if the impedance flag is not present, the prediction output is not generated;
3) if the ratio flag is not available (for example, the patient's body mass index is not known), or if the patient's body mass index is very high, the ratio flag is considered to be always present, and the prediction output is generated based on the impedance flag and the breath flag as described in 1) above;
4) if the breath flag is not available, the breath flag is considered to be always present, and the prediction output is generated based on the impedance flag and the ratio flag; and
5) if the ratio flag and the breath flag are not available, then the prediction output is generated based only on the impedance flag.

As described above, the prediction method operates during the monitoring period, after the baseline values are established. In some cases, it may be determined during the initial monitoring period that an acute decompensated heart failure is likely imminent, and the prediction output may be generated before the baseline values are established. For example, once the patient's predicted impedance $IM_P$ is known and a reading of the patient's actual impedance parameter is available, the prediction output may be generated if the actual impedance parameter reading is below a specified minimum value. The specified minimum value may be set at any suitable value, for example 70% of the patient's predicted impedance $IM_P$, 75%, 80%, 85%, or some other value.

Figure 10:
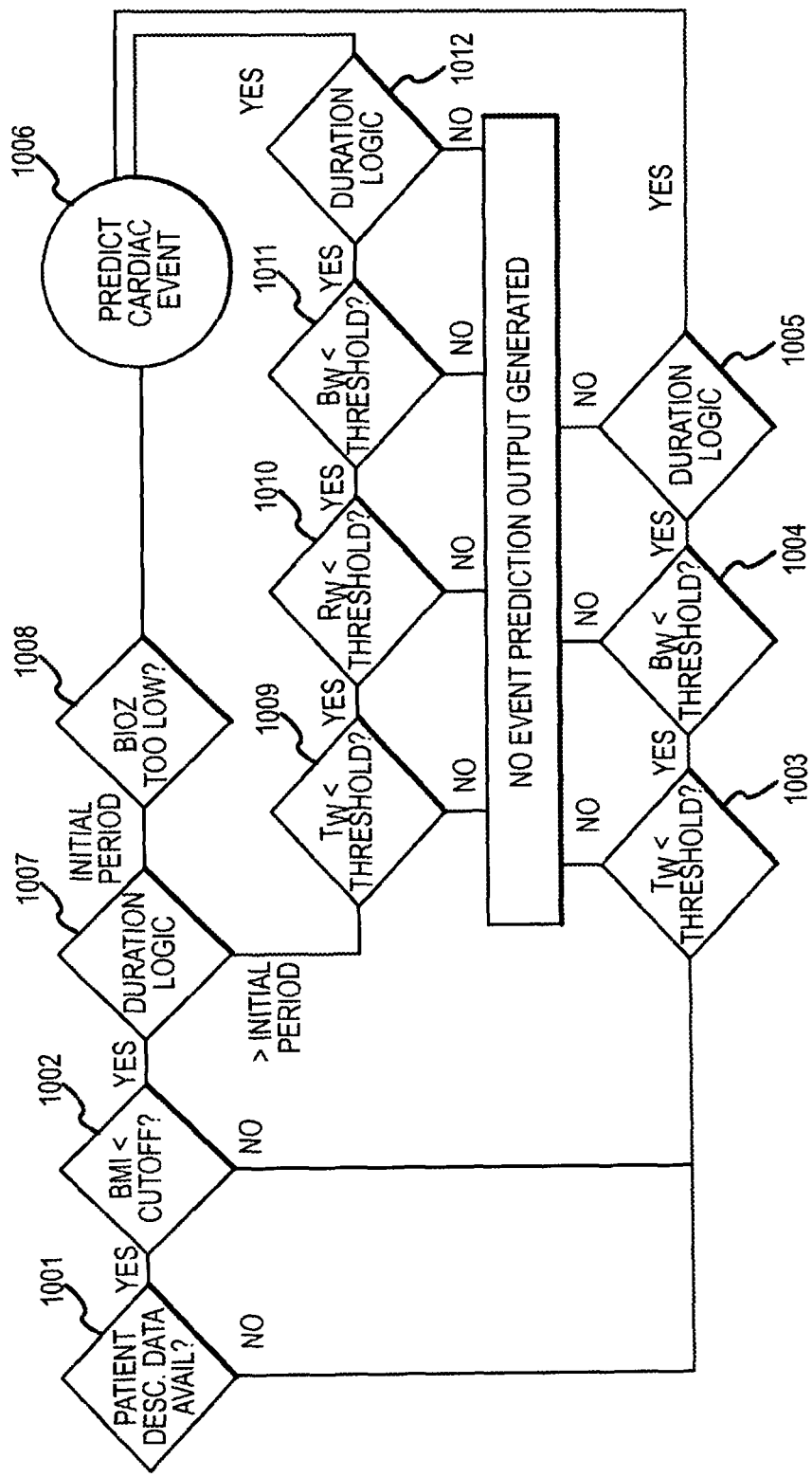
FIG. 10 graphically illustrates event prediction logic according to embodiments.

FIG. 10 graphically illustrates the event prediction logic according to embodiments. The sequence depicted in FIG. 10 may be performed for each window of data gathering. In test 1001, it is determined whether patient descriptive data such as the patient's height, weight, or body mass index is available. If so, the patient's body mass index is checked at test 1002 to see if it is greater than a cutoff value. The cutoff value may be set at any suitably predictive value, for example, 34 kg/m$^2$, 36 kg/m$^2$, 38 kg/m$^2$, 40 kg/m$^2$, or another value. If the patient descriptive data is not available or the patient's body mass index is too high, control passes to test 1003, where the patient's impedance index $T_W$ is tested against the patient's patient-specific impedance change threshold. If the impedance index has not gone below the threshold, then no event prediction output will be generated. Similarly, the patient's breath index $B_W$ is tested in test 1004 against the patient's threshold. If the breath index has not reached the threshold, no event prediction output is generated. Only if both the impedance index and the breath index have gone below their thresholds and impedance and breath flags generated, the flags are checked at test 1005 to see if the flags have been raised for the amounts of time required for event prediction. If not, no event prediction output is generated. But if the duration logic of test 1005 indicates that the flags have been raised for sufficient times, then an event prediction output is generated at 1006.

If tests 1001 and 1002 reveal that patient descriptive data is available and the patient's body mass index is below the cutoff value, then duration logic at test 1007 checks to see if the current reading is within the initial baseline monitoring period. If so, and if the impedance parameter (BIOZ) is too low, as determined at test 1007, then an event prediction output is generated at 1006. If test 1007 reveals that the initial baseline monitoring period has passed, then control passes to tests 1009, 1010, and 1011, where it is determined whether all of the impedance index $T_W$, the ratio index $R_W$, and the breath index $B_W$ have crossed their respective thresholds so that the impedance flag, the ratio flag, and the breath flag have been raised. If any of the flags has not been raised at some point, then no event prediction output is generated. If all of the flags have been raised at least once, then duration logic at tests 1012 tests whether the flags have been raised for sufficient duration and in the correct relationship for event prediction. If not, no event prediction output is generated, but if so, the event prediction output is generated at 1006. Other ways of combining patient information to generate an event prediction output may be envisioned within the scope of the claims.

Experimental Clinical Studies

An experimental clinical study can be conducted on an empirical number of patients to determine empirically parameters of the above described adherent device and processor system so as to adjust impedance based on data of the patient. The empirically determined parameters can be used with programs of the processor system to determine status of the patient, for example to determine deterioration in the status, based on the teachings as described herein.

Body Mass Index Study

FIG. 4 shows a scatter plot of impedance and body mass index measured with an experimental study comprising a measurement population of approximately 200 patients. The study was conducted with an adherent patch device as described above. The data show a correspondence of body mass index with measured impedance, and the correlation has been determined to be statistically significant with a p value less than 0.001. The impedance increased at least about 1 Ohm per BMI unit increased and was shown to be about 2 Ohms per unit BMI increase. These patient population data indicate that an "optimal" bioimpedance value is about 70 Ohms for a patient with a BMI of about 35 and about 50 Ohms for a patient with a BMI of about 25.

Determination and Validation of Prediction Method

In another study, 543 heart failure patients were enrolled. Each of the patients was in New York Heart Association functional class III or IV, had an ejection fraction of 40% or less, and had a recent admission to a hospital for treatment of heart failure. The patients were monitored for 90 days using a multi-sensor system that monitored bioimpedance and other data. Of the 543 patients, 206 were assigned to a development cohort, and data from this cohort were used to develop a prediction method as described above. The method was then applied to data from other 337 patients, to validate the prediction accuracy of the method. Of the 543 patients, 314 completed the study.

Both single-variable and multi-variable prediction methods were evaluated, with the following results achieved in the validation patient population:

| | Sensi-tivity (%) | Speci-ficity (%) | False Positive Rate (Event/ patient-yr.) | Advance Detection Time (Days) |
|---|---|---|---|---|
| Impedance Index | 83 | 40 | 9.4 | |
| Impedance Index and Breath Index | 70 | 77 | 2.3 | |

-continued

| | Sensi-tivity (%) | Speci-ficity (%) | False Positive Rate (Event/ patient-yr.) | Advance Detection Time (Days) |
|---|---|---|---|---|
| Impedance Index and Predicted Impedance | 71 | 74 | 3.2 | |
| Impedance Index, Breath Index, and Predicted Impedance | 65 | 90 | 0.7 | Mean 11.4 +/− 9.0 Median 9.0 Range 2.4 to 33.3 |

Sensitivity is a measure of the method's ability to recognize impending events, and may be defined as the number of true positive predictions divided by the number of cardiac events that occurred in the patient population, that is Sensitivity=#TP/#Events.

Specificity is a measure of the method's ability to correctly recognize that no cardiac event is pending, and may be defined as the number of true negative readings divided by the number of patient records without events, that is Specificity=#TN/#Patient records without events.

The false positive (FP) rate is a measure of the method's tendency to predict a cardiac event when none actually occurs, and may be defined as the number of false positive predictions divided by the total data duration in years, that is FP Rate=#FP/Total data duration.

A true positive may be defined as a prediction output that culminates in a cardiac event, for example a prediction output lasting at least 24 hours and culminating in an acute decompensated heart failure event.

A false positive may be defined as the generation of a prediction output without the predicted event occurring. A prediction output that switches off and is not followed by an event may also be considered a false positive.

A false negative may be defined as a cardiac even that is not preceded by a prediction output within the preceding 24 hours.

A true negative occurs when no prediction output is generated, and no cardiac events occur during the monitoring period.

As can bee seen from the experimental results, multi-parameter prediction results in significantly improved prediction accuracy, as compared with single-parameter prediction, especially in the reduction of the false positive rate.

The above data are exemplary and a person or ordinary skill in the art will recognize many variations and alterations based on the teachings described herein.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A system for predicting a cardiac event of a patient, the system comprising:
    an adherent device attachable to a patient to electronically measure impedance data from the patient;
    an input mechanism for receiving patient descriptive data indicating at least one descriptive characteristic of the patient; and a processor and a tangible memory readable by the processor;

wherein the memory stores instructions that, when executed by the processor, cause the system to:

receive the impedance data;

establish at least one personalized value for the patient based on the impedance data;

receive patient descriptive data indicating at least one descriptive characteristic of the patient;

establish a predicted impedance specific to the patient, based at least in part on the patient descriptive data; and generate, based at least in part on the impedance data, the predicted impedance, and the at least one personalized value, a patient event prediction output predictive of a patient cardiac event.

2. The system of claim 1, wherein the adherent device further comprises:

at least two electrodes in contact with the patient's skin; and an electronics module that measures the impedance between at least two of the electrodes and transmits the impedance data representing the impedance to the processor.

3. The system of claim 2, wherein the adherent device comprises the processor.

4. The system of claim 1, further comprising:

a computer system that comprises the processor; and a communication link over which the impedance data is transmitted from the adherent device to the computer system.

5. The system of claim 4, further comprising an intermediate device that receives the impedance data from the adherent device and relays the impedance data to the computer system.

6. The system of claim 4, wherein the adherent device transmits the impedance data to the computer system at least in part via a wireless link.

7. The system of claim 1, wherein the patient event prediction output is predictive of an acute decompensated heart failure event.

8. The system of claim 1, wherein the instructions, when executed by the processor, further cause the system to:

establish from the impedance data a baseline impedance specific to the patient; and generate the patient event prediction output based at least on part on the relationship of ongoing impedance measurements to the baseline impedance.

9. The system of claim 1, wherein the instructions, when executed by the processor, further cause the system to:

establish from the impedance data a baseline breath parameter specific to the patient; and generate the patient event prediction output based at least on part on the relationship of ongoing measurements of the breath parameter to the baseline breath parameter.

10. The system of claim 1, wherein the instructions, when executed by the processor, further cause the system to:

generate the patient event prediction output based at least on part on the relationship of ongoing measurements of the impedance to the patient's predicted impedance.

11. The system of claim 1, wherein the instructions, when executed by the processor, further cause the system to:

establish from the impedance data a baseline impedance specific to the patient;

establish from the impedance data a baseline breath parameter specific to the patient; and generate the patient event prediction output based at least on part on the relationship of ongoing measurements of the impedance to the baseline impedance, and the relationship of ongoing measurements of the breath parameter to the baseline breath parameter.

12. The system of claim 11, wherein the instructions, when executed by the processor, further cause the system to:

generate the patient event prediction output based at least in part on the relationship of ongoing measurements of the impedance to the patient's predicted impedance.

13. The system of claim 12, wherein the instructions, when executed by the processor, further cause the system to:

compute an impedance index indicative of a change in the impedance relative to the baseline impedance over time;

compute a breath index indicative of a change in the breath parameter relative to the baseline breath parameter over time;

compute a predicted impedance index indicative of a change in the impedance relative to the predicted impedance over time; and compare the impedance index, the breath index, and the predicted impedance index with respective preselected thresholds.

14. The system of claim 13, wherein the instructions, when executed by the processor, further cause the system to:

compute an amount of time for which at least one of the indices has exceeded its respective threshold.

15. The method of claim 14, wherein the instructions, when executed by the processor, further cause the system to generate the patient prediction output predicting a cardiac event when the impedance index and the predicted impedance index have both exceeded their respective thresholds for time periods of preselected duration, and the breath index has exceeded its respective threshold at least once during the time period.

16. The system of claim 1, wherein the patient descriptive data indicate a body composition of the patient, and wherein the instructions, when executed by the processor, cause the system to establish the predicted impedance based at least in part on the indicated body composition of the patient.

17. The system of claim 1, wherein the patient descriptive data comprises a height and weight of the patient, and wherein the instructions, when executed by the processor, cause the system to establish the predicted impedance based at least in part on the height and weight of the patient.

18. The system of claim 1, wherein the instructions, when executed by the processor, cause the system to establish the predicted impedance based at least in part on a body mass index of the patient.

19. A system for predicting a cardiac event of a patient, the system comprising;

an adherent device attachable to a patient to electronically measure impedance data from the patient;

an input mechanism for receiving patient descriptive data indicating at least one descriptive characteristic of the patient; and a processor and a tangible memory readable by the processor;

wherein the memory stores instructions that, when executed by the processor, cause the system to:

receive the impedance data;

receive patient descriptive data indicating at least one descriptive characteristic of the patient:

establish a predicted impedance specific to the patient, based at least in part on the patient descriptive data;

establish from the impedance data a baseline impedance specific to the patient;

compute an impedance index indicative of a change in the impedance relative to the baseline impedance over time;

compare the impedance index with a preselected impedance index threshold;

compute an amount of time for which the impedance index has exceeded the impedance index threshold; and generate, based at least in part on the impedance index and the predicted impedance, a patient event prediction output predictive of a patient cardiac event, only if the impedance index has exceeded the impedance index threshold for at least a preselected time.

* * * * *